(12) United States Patent
Kwon

(10) Patent No.: US 12,133,685 B2
(45) Date of Patent: Nov. 5, 2024

(54) COAXIAL NON-MYDRIATIC MULTISPECTRAL FUNDUS CAMERA USING NEAR-INFRARED RAY ILLUMINATION SOURCE AND VISIBLE RAY ILLUMINATION SOURCE

(71) Applicant: ARK Inc., Busan (KR)

(72) Inventor: Han Jo Kwon, Busan (KR)

(73) Assignee: ARK INC., Busan (KR)

( * ) Notice: Subject to any disclaimer, the term of this patent is extended or adjusted under 35 U.S.C. 154(b) by 1030 days.

(21) Appl. No.: 17/045,319

(22) PCT Filed: Apr. 3, 2019

(86) PCT No.: PCT/KR2019/003936
§ 371 (c)(1),
(2) Date: Oct. 5, 2020

(87) PCT Pub. No.: WO2019/194570
PCT Pub. Date: Oct. 10, 2019

(65) Prior Publication Data
US 2021/0121064 A1    Apr. 29, 2021

(30) Foreign Application Priority Data
Apr. 4, 2018  (KR) .......................... 10-2018-0039225

(51) Int. Cl.
*A61B 3/00* (2006.01)
*A61B 3/15* (2006.01)
*G02B 27/14* (2006.01)

(52) U.S. Cl.
CPC ............ *A61B 3/156* (2013.01); *A61B 3/0008* (2013.01); *A61B 3/154* (2013.01); *G02B 27/14* (2013.01)

(58) Field of Classification Search
CPC .. A61B 3/103; A61B 3/12; A61B 3/14; A61B 3/152; A61B 3/107; A61B 3/10;
(Continued)

(56) References Cited

U.S. PATENT DOCUMENTS

| 7,780,292 B2 * | 8/2010 | Kakuuchi ................ A61B 3/14 351/243 |
| 2011/0051084 A1 * | 3/2011 | Dobashi ................... A61B 3/12 351/206 |

(Continued)

FOREIGN PATENT DOCUMENTS

| JP | 5631450 B2 | 11/2014 |
| JP | 2015-104581 A | 6/2015 |

(Continued)

OTHER PUBLICATIONS

International Search Report for PCT/KR2019/003936 mailed Jul. 11, 2019 from Korean Intellectual Property Office.

*Primary Examiner* — Brandi N Thomas
(74) *Attorney, Agent, or Firm* — Paratus Law Group, PLLC

(57) ABSTRACT

Disclosed is a coaxial non-mydriatic multispectral fundus camera, including: an illumination unit configured to emit light; a diffusion lens configured to diffuse the light incident from the illumination unit; an illumination lens configured to irradiate the light incident from the diffusion lens at a predetermined emission angle; a mirror configured to reflect the light incident from the illumination lens; a polarizing beam splitter configured to transmit P-polarized light of the light incident from the mirror and reflect S-polarized light thereof; an objective lens configured to image a fundus using the light incident from the polarizing beam splitter and then enlarge a returning image of the fundus; a short-range eyepiece lens configured to reduce or enlarge the image of the fundus enlarged by the objective lens; and an imaging (Continued)

device configured to acquire a fundus photograph from the image of the fundus received from the short-range eyepiece lens.

10 Claims, 10 Drawing Sheets

(58) Field of Classification Search
CPC ..... A61B 3/0091; A61B 3/112; A61B 3/0083; A61B 3/0025; A61B 3/0075; A61B 3/145; A61B 3/156; A61B 3/1015; A61B 3/00; A61B 3/102; A61B 3/1035; A61B 3/1241; A61B 3/1208; A61B 3/0008; A61B 3/1025; A61B 3/1173; A61B 5/00; A61B 3/09; A61B 3/1005; A61B 3/117; A61B 3/18; A61B 5/0073; A61B 5/0075; A61B 90/20; A61B 2562/0233; A61B 3/0016; A61B 3/13; A61B 3/135; A61B 3/154; A61B 3/158; A61B 5/0035; A61B 5/0071; A61B 5/0077; A61B 5/1075; A61B 5/14555; A61B 90/36; A61B 2562/0242; A61B 3/0041; A61B 3/0058; A61B 3/024; A61B 3/028; A61B 3/032; A61B 3/132; A61B 5/0002; A61B 5/0059; A61B 5/0068; A61B 5/489; A61B 5/6824; A61B 5/7207; A61F 2009/00872; A61F 2009/00853; A61F 2009/00887; A61F 9/00827; A61F 2009/00846; A61F 2009/0087; A61F 2009/0088; A61F 2009/00882; A61F 2009/00889; A61F 9/008; A61F 9/00825; A61F 9/00829; A61F 2009/00842; A61F 2009/00848; A61F 2009/00868; A61F 9/007; A61F 9/00736; A61F 9/0081; A61F 9/00831; A61F 9/00834; A61F 9/013; A61F 2009/00863; G02B 2027/0132; G02B 27/0172; G02B 27/14; G02B 21/0012; G02B 25/00; G02B 25/004; G02B 27/017; G02B 27/0176; G02B 5/30; G02B 7/002; G02B 15/10; G02B 27/10; G02B 27/106; G02B 13/0095; G02B 17/02; G02B 17/0896; G02B 2027/011; G02B 2027/0138; G02B 21/0024; G02B 21/008; G02B 23/10; G02B 23/12; G02B 23/18; G02B 7/12

See application file for complete search history.

(56) References Cited

U.S. PATENT DOCUMENTS

2011/0267583 A1* 11/2011 Hayashi .................. A61B 3/14
356/479
2014/0058367 A1* 2/2014 Dantus .................. H01S 3/005
606/4

FOREIGN PATENT DOCUMENTS

JP          5835264 B2      12/2015
JP          2017-512992 A    5/2017
KR     10-2013-0099113 A    9/2013

* cited by examiner

λ = 740nm    λ = 850nm    λ = 940nm

B  Nidek ACF330
MYDRIATIC FUNDUS CAMERA

A  PRESENT INVENTION

COAXIAL NON-MYDRIATIC MULTISPECTRAL FUNDUS CAMERA USING NEAR-INFRARED RAY ILLUMINATION SOURCE AND VISIBLE RAY ILLUMINATION SOURCE

CROSS-REFERENCE TO PRIOR APPLICATIONS

This application is a National Stage Patent Application of PCT International Patent Application No. PCT/KR2019/003936 (filed on Apr. 3, 2019) under 35 U.S.C. § 371, which claims priority to Korean Patent Application No. 10-2018-0039225 (filed on Apr. 4, 2018), which are all hereby incorporated by reference in their entirety.

BACKGROUND

The present invention relates to a fundus camera which is a kind of diagnostic equipment for ophthalmic examination, and more particularly, to a fundus camera which is capable of easily illuminating a fundus in a non-mydriatic state using a narrowband illumination source and then easily recording light reflected from the fundus in the non-mydriatic state through an imaging device using a visible ray illumination source.

In the conventional mydriatic fundus cameras, after mydriasis (pupil dilation) using a mydriatic, a fundus is illuminated using an illumination source in a visible ray band, and light reflected from the fundus is recorded using a film camera or an imaging device. In the conventional non-mydriatic color fundus camera, after a fundus in a non-mydriatic state is imaged using a near-infrared ray illumination source, a focus is adjusted, an adjustment is performed to align an imaging device with the fundus, and then, a fundus photograph is acquired using a xenon flash tube or other types of visible ray source to implement a non-mydriatic function. More specifically, in the conventional non-mydriatic color fundus camera, a near-infrared ray illumination source was disposed around an objective lens, and a focus and a viewing angle before photographing were adjusted using light which is near-infrared ray illumination that passed through a sclera or a cornea and was reflected from a retina after. That is, an off-axis illumination method is adopted in which the near-infrared ray illumination is not aligned with an axis of an imaging device.

In general, in a bottom layer of a retina, there is a cell layer called a retinal pigment epithelium and including abundant melanin. The melanin has a property of absorbing blue light to red light having a visible ray band wavelength. The property helps the retina to react sensitively to light in a visible ray band, but for the same reason, there is a disadvantage in that it is not possible to check a choroidal structure or blood vessel layer under the retina using light in a visible ray band in detail.

Since visual cells are mainly located in a subretinal layer, blood is not supplied to a retina. Thus, the retina receives oxygen from a choroidal capillary under the retina to maintain cell activity. Therefore, when a problem occurs in the choroidal capillary or a choroid, the supply of oxygen to the retina becomes difficult, and the retina, retinal pigment epithelium, and choroidal capillary enter a hypoxic state, inflammatory materials such as angiogenesis factors and cytokines are secreted, and neovascularization is caused. Thus, vision is damaged by bleeding and an exudation in a macula.

Retinal diseases caused by a choroidal lesion are diverse. Currently, macular degeneration, which is the second cause of blindness in adult retinal patients in Korea, is a disease in which a retina is damaged due to neovascularization generated in a choroid. Myopic choroidal neovascularization, which is common in Asians, is also a disease in which, after a choroid is mechanically stretched and ruptured, neovascularization is generated in a healing process, and thus, bleeding occurs in a subretinal layer, whereby central vision is rapidly degraded.

In addition, a choroidal damage and choroidal neovascularization due to a face region or eyeball impact caused by a laser or trauma are also mainly caused by the choroidal lesion. Furthermore, a choroiditis caused by an inflammation of a choroid, Vogt-Koyanagi-Harada disease, sympathetic endophthalmitis, white dot syndrome, and ocular syphilis caused by infection of the choroid are also major ophthalmic diseases that invade the choroid.

In order to discriminate these diseases from purely retinal diseases, for the reason above, there is a limitation in diagnosing the diseases using a visible ray mydriatic color fundus camera. In the past, a choroidal lesion has been discriminated using an indocyanine green angiography device in an ophthalmic field, which has disadvantages in that costs are high, and a contrast agent should be injected into a vein. Recently, a choroidal lesion is confirmed using an optical coherence tomography device, which also has disadvantages in that the device is very expensive and only a narrow range of lesions can be identified.

SUMMARY

The present invention is directed to providing a non-mydriatic fundus camera in which a near-infrared light source and a visible light source are disposed on the same illumination axis, thereby 1) acquiring a clear near-infrared ray fundus photograph, 2) reducing phototoxicity by reducing a price and energy of light transferred to an eyeball using a small number of the near-infrared ray illumination sources, and 3) capturing a color fundus photograph, of which a viewing angle and an image match those of an image of a fundus imaged using a near-infrared ray.

In addition, the present invention is directed to providing a non-mydriatic fundus camera in which a visible light source and a near-infrared light source are provided to be replaceable, thereby using near-infrared light sources and visible light sources having various wavelengths.

Furthermore, the present invention is directed to providing a fundus camera capable of removing various types of internal reflections and acquiring a clear fundus photograph.

The technical objects that can be achieved through the present invention are not limited to what has been particularly described hereinabove and other technical objects not described herein will be more clearly understood by persons skilled in the art from the following detailed description.

According to the present invention, a coaxial non-mydriatic multispectral fundus camera, which uses a near-infrared ray illumination source and a visible ray illumination source, includes an illumination unit (10) configured to emit light, a diffusion lens (20) configured to diffuse the light incident from the illumination unit (10), an illumination lens (30) configured to irradiate the light incident from the diffusion lens (20) at a predetermined emission angle, a mirror (40) configured to reflect the light incident from the illumination lens (30), a polarizing beam splitter (50) configured to transmit P-polarized light of the light incident from the mirror (40) and reflect S-polarized light thereof, an objective lens (60) configured to image a fundus using the light incident from the polarizing beam splitter (50) and then enlarge a returning image of the fundus, a short-range eyepiece lens (70) configured to reduce or enlarge the image of the fundus enlarged by the objective lens (60), and an imaging device (100) configured to acquire a fundus photograph from the image of the fundus received from the short-range eyepiece lens (70), wherein the illumination unit (10) includes a near-infrared ray illumination source (11) configured to emit a near-infrared ray, a visible ray illumination source (12) configured to emit a visible ray, and a non-polarizing beam splitter (13) configured to allow the near-infrared ray emitted from the near-infrared ray illumination source (11) and the visible ray emitted from the visible ray illumination source (12) to be emitted coaxially.

In the coaxial non-mydriatic multispectral fundus camera using a near-infrared ray illumination source and a visible ray illumination source, (i) when, with respect to the non-polarizing beam splitter (13), the near-infrared ray illumination source (11) is disposed perpendicularly to an illumination axis and the visible ray illumination source (12) is disposed on the illumination axis, and for example, when a non-polarizing beam splitter having a transmission-to-reflection ratio of 5:5 is used, the non-polarizing beam splitter (13) may reflect 50% of near-infrared rays emitted from the near-infrared ray illumination source (11) to transfer the reflected near-infrared rays to the illumination axis and may transmit the remaining 50% of the near-infrared rays to be absorbed at a boundary of the beam splitter, and the non-polarizing beam splitter (13) may transmit 50% of visible rays emitted from the visible ray illumination source (12) to transfer the transmitted visible rays to the illumination axis and may reflect the remaining 50% of the visible rays to be absorbed at the boundary of the beam splitter.

(ii) When, with respect to the non-polarizing beam splitter (13), the near-infrared ray illumination source (11) is disposed on the illumination axis and the visible ray illumination source (12) is disposed perpendicularly to the illumination axis, and for example, when a non-polarizing beam splitter having a transmission-to-reflection ratio of 5:5 is used, the non-polarizing beam splitter (13) may transmit 50% of the near-infrared rays emitted from the near-infrared ray illumination source (11) to transfer the transmitted near-infrared rays to the illumination axis and may reflect the remaining 50% of the near-infrared rays to be absorbed at the boundary of the beam splitter, and the non-polarizing beam splitter (13) may reflect 50% of the visible rays emitted from the visible ray illumination source (12) to transfer the reflected visible rays to the illumination axis and may transmit the remaining 50% of the visible rays to be absorbed at the boundary of the beam splitter.

In the coaxial non-mydriatic multispectral fundus camera using a near-infrared ray illumination source and a visible ray illumination source, the near-infrared ray illumination source (11) may be a light-emitting diode or a narrowband single wavelength laser which emits a narrowband near-field ray in a range of 700 nm to 1,000 nm.

In the coaxial non-mydriatic multispectral fundus camera using a near-infrared ray illumination source and a visible ray illumination source, the visible ray illumination source (12) may be a narrowband visible light source or a narrowband single wavelength laser which emits a narrowband visible ray in a range of 400 nm to 700 nm, or a visible light-emitting diode having a continuous spectrum ranging from 400 nm to 700 nm.

In the coaxial non-mydriatic multispectral fundus camera using a near-infrared ray illumination source and a visible ray illumination source, the near-infrared ray illumination source (11) may be provided with a plurality of near-infrared ray illumination sources (11) in different bands, and each of the plurality of near-infrared ray illumination sources (11) may be detachable from the coaxial non-mydriatic multispectral fundus camera so that one of the plurality of near-infrared ray illumination sources (11) may be replaced with another one of the plurality of near-infrared ray illumination sources (11).

In the coaxial non-mydriatic multispectral fundus camera using a near-infrared ray illumination source and a visible ray illumination source, the visible ray illumination source (12) may be provided with a plurality of visible ray illumination sources (12) in different bands, and each of the plurality of visible ray illumination sources (12) may be detachable from the coaxial non-mydriatic multispectral fundus camera so that one of the plurality of visible ray illumination sources (12) may be replaced with another one of the plurality of visible ray illumination sources (12).

In the coaxial non-mydriatic multispectral fundus camera using a near-infrared ray illumination source and a visible ray illumination source, the coaxial non-mydriatic multispectral fundus camera may further include an illumination source case (90) which includes a housing in which the near-infrared ray illumination source (11) is embedded and is detachable from the coaxial non-mydriatic multispectral fundus camera, wherein an opening is formed in one surface of the housing so that light from the near-infrared ray illumination source (11) is emitted from the opening to an illumination axis. The illumination source case (90), which is mounted with one of a plurality of near-infrared ray illumination sources (11) and is mounted in the coaxial non-mydriatic multispectral fundus camera, may be replaced with the illumination source case (90) mounted with still another one of the plurality of near-infrared ray illumination sources (11).

In the coaxial non-mydriatic multispectral fundus camera using a near-infrared ray illumination source and a visible ray illumination source, the coaxial non-mydriatic multispectral fundus camera may further include an illumination source case (90) which includes a housing in which the visible ray illumination source (12) is embedded and is detachable from the coaxial non-mydriatic multispectral fundus camera, wherein an opening is formed in one surface of the housing so that light from the visible ray illumination source (12) is emitted from the opening to an illumination axis. The illumination source case (90), which is mounted with one of the plurality of visible ray illumination sources (12) and is mounted in the coaxial non-mydriatic multispectral fundus camera, may be replaced with the illumination source case (90) mounted with still another one of the plurality of visible ray illumination sources (12).

In the coaxial non-mydriatic multispectral fundus camera using a near-infrared ray illumination source and a visible ray illumination source, the coaxial non-mydriatic multispectral fundus camera may further include at least one of a first linear polarizing filter (81) configured to transmit only the P-polarized light and provided between the illumination unit (10) and the polarizing beam splitter (50) and a second linear polarizing filter (82) provided between the polarizing beam splitter (50) and the imaging device (100).

In the coaxial non-mydriatic multispectral fundus camera using a near-infrared ray illumination source and a visible ray illumination source, the coaxial non-mydriatic multispectral fundus camera may further include a first linear polarizing filter (81) configured to transmit only the P-polarized light and provided between the illumination unit (10)

and the polarizing beam splitter (50), and a second linear polarizing filter (82) provided between the polarizing beam splitter (50) and the imaging device (100).

The first linear polarizing filter (81) and the second linear polarizing filter (82) may have the same polarity to transmit only high-purity P-polarized light.

According to the present invention, a method of acquiring a fundus photograph using the a fundus camera includes setting a near-infrared ray illumination source (11) to be turned on and setting a visible ray illumination source (12) to be turned off (S1), imaging a fundus using the near-infrared ray illumination source (11) and adjusting a focus and a viewing angle (S2), acquiring a near-field ray fundus photograph by photographing the fundus in a state in which the fundus is imaged using the near-infrared ray illumination source (11) (S3), setting the near-infrared ray illumination source (11) to be turned off and setting the visible ray illumination source (12) to be turned on (S4), and acquiring a visible ray fundus photograph by photographing the fundus in a state in which the fundus is imaged using the visible ray illumination source (12) (S5).

In the method of acquiring a fundus photograph using a fundus camera, the method may further include setting both the near-infrared ray illumination source (11) and the visible ray illumination source (12) to be turned off so that the fundus camera enters a standby mode (S6).

By the technical solution, according to the present invention, not only a visible ray illumination source but also a near-infrared ray illumination source are positioned coaxially, thereby 1) acquiring a clear near-infrared ray fundus photograph, 2) reducing phototoxicity by reducing a price and energy of light transferred to an eyeball using a single near-infrared ray illumination source, and 3) capturing a color fundus photograph, of which a viewing angle and a focus match those of an image of a fundus imaged using a near-infrared ray.

In addition, according to the present invention, in a fundus camera using coaxial illumination, various types of internal reflections can be removed and a clear fundus photograph can be acquired using a combination of a polarizing beam splitter and two linear polarizing filters.

In addition, according to the present invention, a near-infrared ray illumination source and a visible ray illumination light source are provided to have various different bands and be easily replaceable, thereby acquiring fundus photographs having various wavelengths and a fundus photograph suitable for each lesion.

Furthermore, a fundus can be effectively photographed in a non-mydriatic state and at a wide angle without an expensive optical device or an expensive laser scanner-based lighting device so that the present invention can be usefully used for ophthalmologic treatment.

In addition, the present invention can be usefully used in photographing a fundus of an animal or in photographing a fundus of a child with whom cooperation is difficult.

In addition, a conventional non-mydriatic fundus camera adopts an off-axis illumination method in which near-infrared ray illumination is not aligned with an axis of an imaging device. However, the present invention is different from the conventional non-mydriatic fundus camera in that a near-infrared ray illumination source and a visible ray illumination source are positioned coaxially, thereby 1) acquiring a clear near-infrared ray fundus photograph, 2) reducing phototoxicity by reducing a price and energy of light transferred to an eyeball using a small number of the near-infrared ray illumination sources, and 3) capturing a color fundus photograph, of which a viewing angle and an image match those of an image of a fundus imaged using a near-infrared ray.

BRIEF DESCRIPTION OF THE DRAWINGS

FIG. 17A is a flowchart of sequentially acquiring a near-infrared ray fundus photograph and a visible ray fundus photograph in a standby mode, and FIG. 17B shows the near-infrared ray fundus photograph and the visible ray fundus photograph acquired in operations of the flowchart of FIG. 17B.

DETAILED DESCRIPTION

Figure 1:
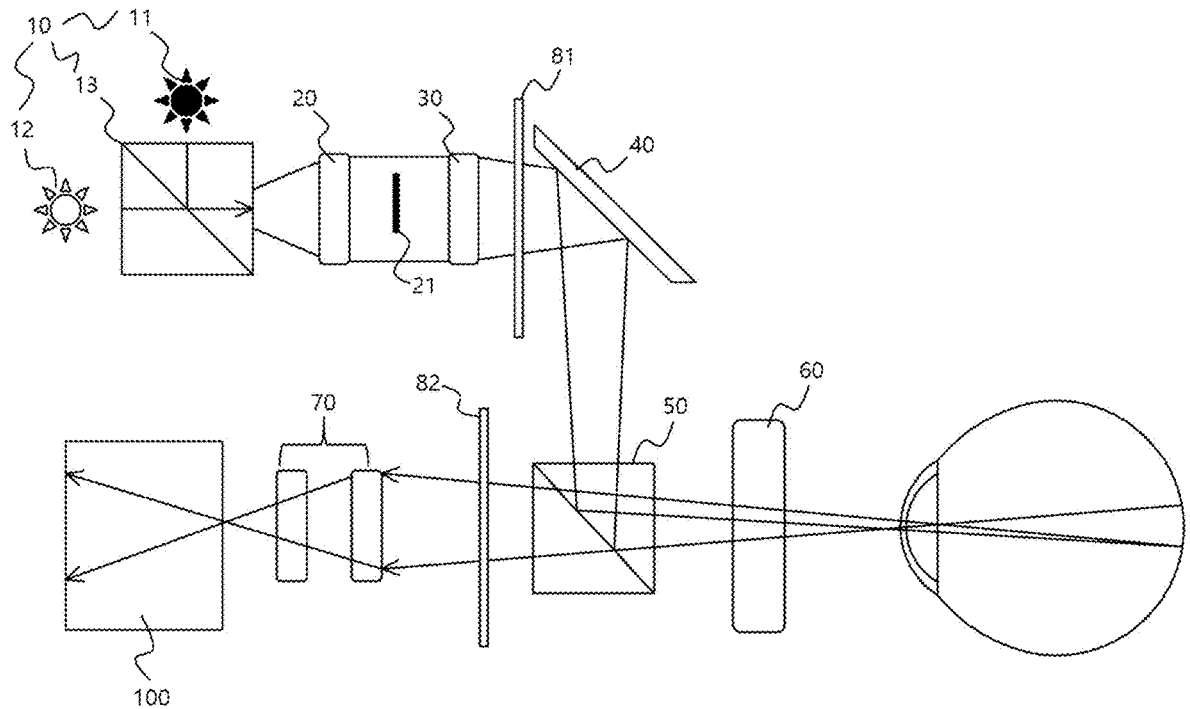
FIG. 1 is a diagram illustrating a non-mydriatic fundus camera including a near-infrared ray illumination source (11), a visible ray illumination source (12), and a non-polarizing beam splitter (13) according to one embodiment of the present invention.

Hereinafter, as a type of fundus camera, which is a kind of diagnostic equipment for ophthalmic examination, a non-mydriatic fundus camera, in which an illumination source configured to emit light having a near-infrared wavelength is added to illuminate a fundus in a non-mydriatic state and to perform near-infrared fundus photographing first, and then, an illumination source in a visible ray band is operated to sequentially record visible ray fundus photographs, that is, a coaxial non-mydriatic multispectral fundus camera using a near-infrared ray illumination source and a visible ray illumination source according to the present invention will be described in detail. The accompanying drawings show an exemplary configuration of the present invention and are merely provided to describe the present invention in more detail, and the scope of the present invention is not limited by the accompanying drawings.

In addition, the same or similar reference numerals are given to the same or corresponding components regardless of reference numerals, of which redundant explanations will be omitted, and for convenience of description, the size and shape of each constituent member as shown may be exaggerated or reduced.

Specific details including the object, solution, and effect of the present invention are included in the following description and the accompanying drawings. The advantages and features of the present invention and a method of achieving the advantages and features will be clarified through embodiments which are described below with reference to the accompanying drawings.

As shown in FIG. 1, the coaxial non-mydriatic multispectral fundus camera using a near-infrared ray illumination source and a visible ray illumination source according to the present invention (hereinafter, referred to "non-mydriatic fundus camera" or "fundus camera") may include an illumination unit 10, a diffusion lens 20, an illumination lens 30, a mirror 40, a polarizing beam splitter 50, an objective lens 60, and a short-range eyepiece lens 70 and may additionally include a linear polarizing filter 80.

First, the illumination unit 10 includes a near-infrared ray illumination source 11, a visible ray illumination source 12, and a non-polarizing beam splitter 13.

The near-infrared ray illumination source 11 may be, for example, an illumination source which emits a near-infrared ray having a center wavelength ranging from 700 nm to 1000 nm. Furthermore, the near-infrared ray illumination source 11 may be, for example, a light-emitting diode or a narrowband single wavelength laser which has an emission center wavelength in a near-infrared band.

A near-infrared ray emitting diode 11 usable in the fundus camera according to the present invention may have a center wavelength of, for example, 740 nm, 760 nm, 800 nm, 810 nm, 850 nm, or 940 nm and have a beam width, for example, ranging from 10 nm to 50 nm, but the present invention is not limited thereto. According to various environments and conditions in which the present invention is implemented, various light-emitting diodes having various center wavelengths may be used as the near-infrared ray illumination source 11.

Figure 9:
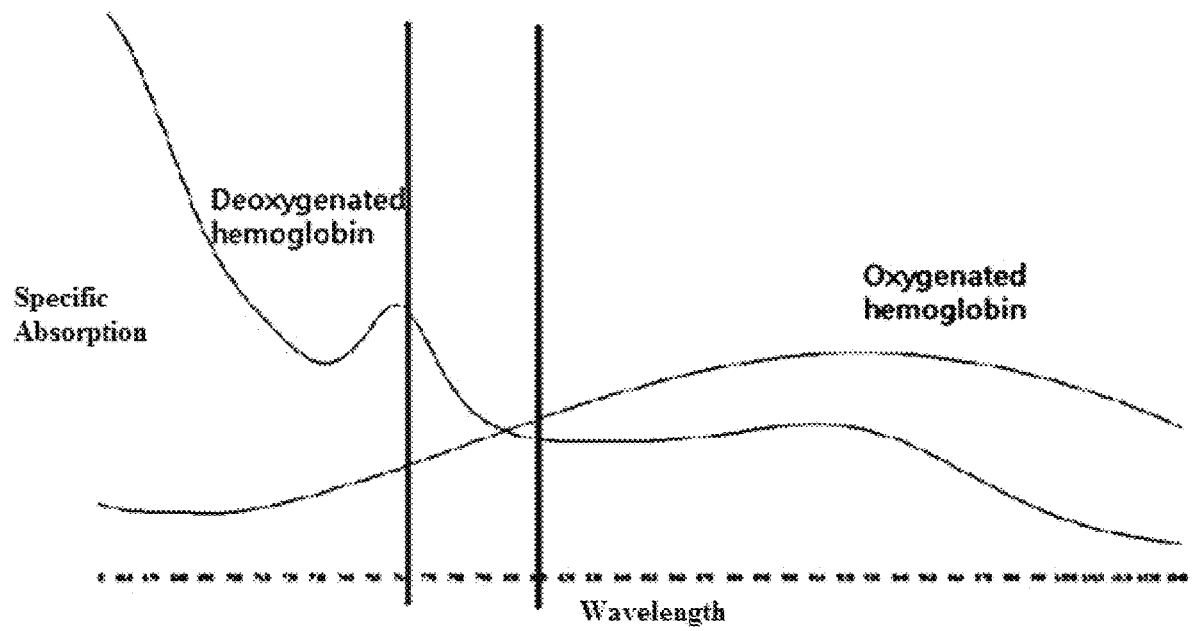
FIG. 9 is a graph showing absorption wavelengths of oxygenated hemoglobin (red line) and deoxygenated hemoglobin (blue line) in a choroidal blood flow.

In other words, the near-infrared ray illumination source 11 may be selected from illumination sources having various wavelengths according to the purpose of examination. First, as shown in FIG. 9, wavelengths in a near-infrared band, which are absorbed by oxidized hemoglobin and deoxygenated hemoglobin of a choroid, are different. The deoxygenated hemoglobin of the choroid absorbs more infrared rays in a band of 800 nm or less than the oxidized hemoglobin.

Accordingly, a choroidal artery and a choroidal arteriole are photographed brighter than a choroidal vein or venule with light having a central wavelength ranging from 700 nm to 800 nm. In this case, in order to check the structure or abnormality of the choroidal artery and arteriole, a near-infrared light source having a band around 750 nm may be selected.

In addition, when light having a wavelength of 800 nm or more is used, such an absorption pattern is reversed so that the choroidal vein or choroidal venule is photographed brighter than the choroidal artery or arteriole. Accordingly, light having a wavelength ranging from 800 nm to 900 nm may be usefully utilized to observe the choroidal vein or choroidal venule.

Furthermore, since light having a wavelength of 900 nm or more is hardly absorbed even by melanin, all structures of the choroid may be observed, and in particular, the light having a wavelength of 900 nm or more may be suitable for observing a choroidal capillary.

Meanwhile, light having a wavelength of 1,000 nm or more departs from a near-infrared ray (NIR) band and corresponds to a short-wave infrared ray (SWIR) region. A charge coupled device (CCD) currently commercialized as an InGaAs CCD has the maximum pixel number of 1 M pixels and is very expensive, and little is known about what information is clinically provided by fundus photographing in an SWIR region. In addition, since light having a wavelength of about 1,000 nm or more begins to be rapidly absorbed by a vitreous body, in order to image the fundus, a very strong output illumination source is required, and the costs are high. In particular, since the very strong output illumination source raises a temperature of the vitreous body, it is also necessary to verify whether the very strong output illumination source is useful for a human body. In addition, even in a conventional monochrome CCD, photon efficiency of an infrared ray having a wavelength of 1,200 nm or more is also rapidly decreased, and a signal ratio instead of noise of an image is rapidly increased. Therefore, obtaining information by imaging a fundus using light having a wavelength of 1,000 nm or more is not suitable for the purpose of this development.

The visible ray illumination source 12 may be, for example, a narrowband visible light source or a narrowband single wavelength laser which emits a narrowband visible ray in a range of 400 nm to 700 nm, or a visible ray-emitting diode having a continuous spectrum ranging from 400 nm to 700 nm.

In addition, the non-polarizing beam splitter 13 allows an NIR emitted from the near-infrared ray illumination source 11 and a visible ray emitted from the visible ray illumination source 12 to be transferred along the same illumination axis, that is, coaxially. For example, when, with respect to the non-polarizing beam splitter 13, the near-infrared ray illumination source 11 is disposed perpendicularly to an illumination axis (that is, an axis extending to the diffusion lens 20, the illumination lens 30, and the mirror 40 to be described below) and the visible ray illumination source 12 is disposed on the illumination axis, the non-polarizing beam splitter 13 reflects an NIR emitted from the near-infrared ray illumination source 11 and transmits a visible ray emitted from the visible ray illumination source 12. On the contrary, when, with respect to the non-polarizing beam splitter 13, the near-infrared ray illumination source 11 is disposed on the illumination axis and the visible ray illumination source 12 is disposed perpendicularly to the illumination axis, the non-polarizing beam splitter 13 transmits an NIR emitted from the near-infrared ray illumination source 11 and reflects a visible ray emitted from the visible ray illumination source 12.

Figure 8:
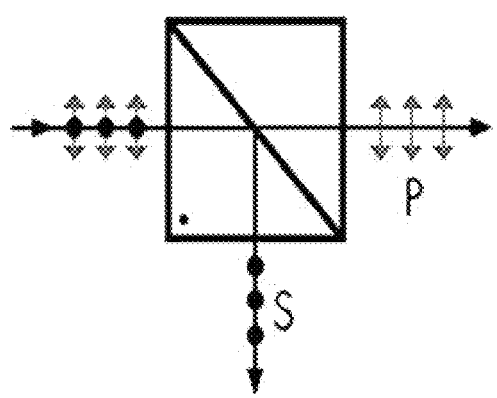
FIG. 8 shows a diagram (FIG. 8A) illustrating a principle of a polarizing beam splitter (50) and a diagram (FIG. 8B) illustrating a principle of a non-polarizing beam splitter (13).
Figure 8:
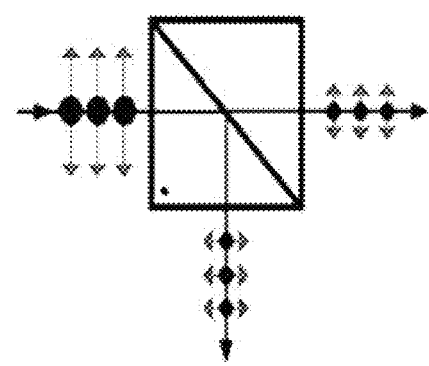

The non-polarizing beam splitter 13 may be an optical component corresponding to FIG. 8B and may not be significantly affected by a polarization state. The non-polarizing beam splitter 13 may be an optical device which transmits a half of incident light and reflects the other half thereof, and a transmission-to-reflection ratio thereof may be variously adjusted to be 1:9, 2:8, 5:5, or the like. Energy of a visible ray and energy of an NIR which are irradiated may be changed according to a transmission-to-reflection ratio, and for example, the fundus camera may be implemented using a non-polarizing beam splitter having a transmission-to-reflection ratio of 5:5. As a transmission ratio of a visible ray is increased, a visible ray fundus photograph may be acquired by a shorter exposure, but a transmission ratio of energy of an NIR is decreased, and thus, a longer exposure is required when a near-infrared ray fundus photograph is acquired. Accordingly, when illumination energy of an NIR and emission energy of a visible ray are the same, the fundus camera of the present invention may be implemented using, for example, a non-polarizing beam splitter having a transmission-to-reflection ratio of 5:5. On the other hand, in the case of an inexpensive imaging device having low photon efficiency in a visible ray band, the fundus camera of the present invention may be implemented using a non-polarizing beam splitter, of which a transmission ratio of an NIR to a visible ray is 3:7.

For example, when a non-polarizing beam splitter having a transmission-to-reflection ratio of 5:5 is used, and when, with respect to the non-polarizing beam splitter 13, the near-infrared ray illumination source 11 is disposed perpendicularly to the illumination axis, and the visible ray illumination source 12 is disposed on the illumination axis, the non-polarizing beam splitter 13 may reflect 50% of NIRs emitted from the near-infrared ray illumination source 11 to transfer the reflected NIR to the illumination axis and may transmit the remainder of the NIR to be absorbed at a boundary of the beam splitter. In addition, the non-polarizing beam splitter 13 may transmit 50% of visible rays emitted from the visible ray illumination source 12 to transfer the transmitted visible ray to the illumination axis and may reflect the remaining 50% of the visible rays to be absorbed at the boundary of the beam splitter.

In addition, for example, when a non-polarizing beam splitter having a transmission-to-reflection ratio of 5:5 is used, when, with respect to the non-polarizing beam splitter 13, the near-infrared ray illumination source 11 is disposed on the illumination axis, and the visible ray illumination source 12 is disposed perpendicularly to the illumination axis, the non-polarizing beam splitter 13 may transmit 50% of NIRs emitted from the near-infrared ray illumination source 11 to transfer the transmitted NIR to the illumination axis and may reflect the remaining 50% of the NIRs to be absorbed at a boundary of the beam splitter. In addition, the non-polarizing beam splitter 13 may reflect 50% of visible rays emitted from the visible ray illumination source 12 to transfer the reflected visible rays to the illumination axis and may transmit the remaining 50% of the visible rays to be absorbed at the boundary of the beam splitter Meanwhile, as the non-polarizing beam splitter 13, any type of a non-polarizing beam splitter, such as a non-polarizing beam splitter formed in the form of a film, a non-polarizing beam splitter made of a glass material, or a cubic non-polarizing beam splitter, may be used. A change in type of the non-polarizing beam splitter as described above does not significantly affect performance of the fundus camera.

In summary, the fundus camera according to the present invention may be implemented in such a manner that the illumination unit 10 includes the near-infrared ray illumination source 11, the visible ray illumination source 12, and the non-polarizing beam splitter 13, and after a focus and a viewing angle are adjusted by first illuminating a fundus in a non-mydriatic state using the near-infrared ray illumination source 11 configured to emit a near-infrared wavelength, a button or device, which instructs a color fundus photograph to be acquired, is turned on to perform visible ray fundus photographing in the non-mydriatic state and then record the acquired color fundus photograph. In this case, the non-polarizing beam splitter 13 allows an NIR emitted from the near-infrared ray illumination source 11 and a visible ray emitted from the visible ray illumination source 12 to be transferred coaxially.

Next, the diffusion lens 20 diffuses light incident from the illumination unit 10. The diffusion lens 20 may include a central imaging mask 21 and thus adjust light using the central imaging mask 21.

Figure 13:
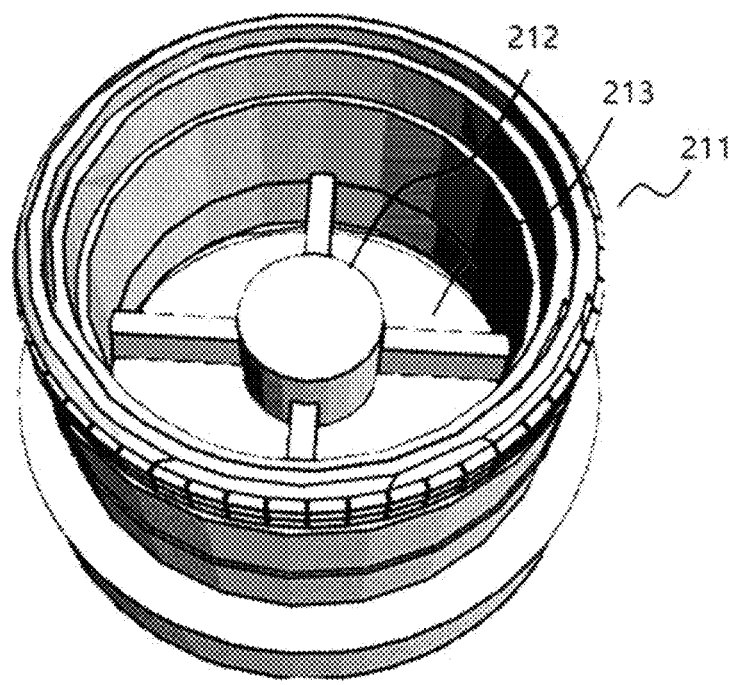
FIG. 13 is a diagram illustrating a masking structure (211) used instead of a central imaging mask (21) to block a central portion.

The central imaging mask 21 is a device for reducing light incident on a coaxial center so as to minimize a corneal reflex. The minimum size of the central imaging mask 21 varies according to a focal length of the objective lens 60 but may generally range from 2.0 mm to 5.0 mm. Under such conditions, the central imaging mask 21 is a key device which prevents light from being incident around an apical convex surface of a central part of a cornea. The central imaging mask 21 may be attached to a front or rear surface of the diffusion lens 20 in a sticky manner. A mark may be marked on a central portion of the diffusion lens 20 using an oil-based pen or a water-based pen, or as shown in FIG. 13, the central portion may be blocked using a masking structure 211.

The masking structure 211 includes a central mask 212 and a spider portion 213 for supporting the central mask 212. The spider portion 213 may be variously designed to have one blade to four blades. As the number of the blades of the spider portion 213 is increased, stability is increased, but there is a problem in that an amount of light is decreased and a diffraction image occurs.

Subsequently, the illumination lens 30 irradiates light incident from the diffusion lens 20 at a predetermined emission angle. The light incident from the diffusion lens 20 is more clearly and constantly emitted by the illumination lens 30.

Next, the mirror 40 reflects light incident from the illumination lens 30. The mirror 40 is a structure required for positioning illumination coaxially with a camera and does not affect optical performance of the fundus camera.

When the illumination is arranged perpendicularly to the camera, the mirror 40 is not required. In addition, when one or more illumination units 10 including a visible ray and an NIR are provided, two light beams having different properties may be incident on the polarizing beam splitter using one beam splitter and two different illumination units 10 instead of the mirror 40.

A direction of the light incident from the illumination lens 30 is changed to emit the light to the polarizing beam splitter 50 to be described below.

Next, the polarizing beam splitter 50 transmits P-polarized light and reflects S-polarized light from light incident from the mirror 40.

More specifically, as shown in FIG. 8A, light corresponding to P-polarized light and light corresponding to S-polarized light are mixed in all light beams. The polarizing beam splitter 50 transmits the light corresponding to the P-polarized light and reflects the light corresponding to the S-polarized light along a 90° bent portion of an optical axis. Meanwhile, as shown in FIG. 8B, the same principle as the polarizing beam splitter 50 is not applied to the non-polarizing beam splitter.

The polarizing beam splitter 50 may be made of a very thin film material or a single square material or a rectangular or circular glass material, and a cubic polarizing beam splitter 50, in which two prisms are combined, may be used. In particular, the cubic polarizing beam splitter 50 in which two prisms are combined has an advantage in that a clear image may be acquired because light refracted on a boundary and then incident on an optical axis again is small.

Next, the linear polarizing filter 80 is provided to have a linear shape and filters the light before reaching the polarizing beam splitter 50 so as to transmit only the P-polarized light. More specifically, the linear polarizing filter 80 may be provided such that the P-polarized light is most transmitted along the polarizing beam splitter 50 and thus only light deflected to a pure P-pole is transmitted.

The linear polarizing filter 80 is provided with a first linear polarizing filter 81 and a second linear polarizing filter 82.

The first linear polarizing filter 81 is provided between the illumination unit 10 and the polarizing beam splitter 50. In a direction closer to the illumination unit 10, the size of the first linear polarizing filter 81 may be reduced, and the total cost of the fundus camera manufactured according to the present invention may be reduced.

As one embodiment, as shown in FIG. 1, the first linear polarizing filter 81 may be provided between the illumination lens 30 and the mirror 40. When the first linear polarizing filter 81 is provided between the illumination lens 30 and the mirror 40, the first linear polarizing filter 81 may be installed such that only the S-polarized light is incident on the mirror 40. Thus, the first linear polarizing filter 81 may be provided such that the P-polarized light, of which a phase is shifted by 90°, is incident on the polarizing beam splitter 50, and the P-polarized light is transferred to the objective lens 60 the most.

Figure 2:
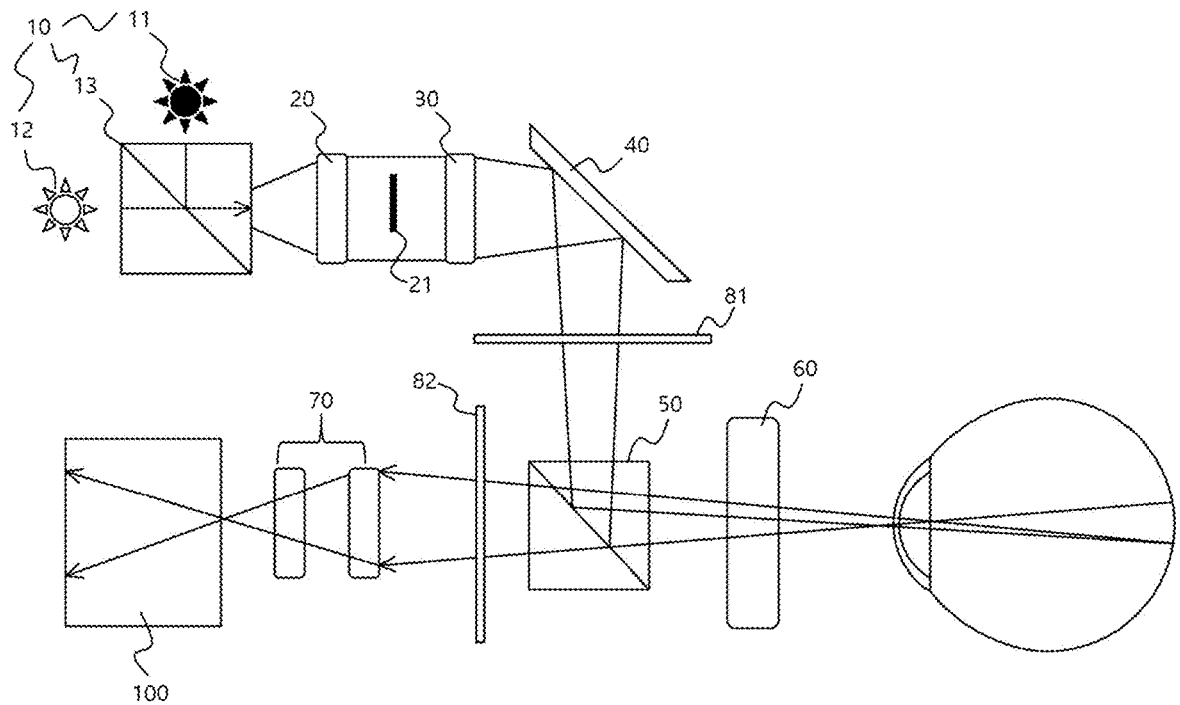
FIG. 2 is a view illustrating an example in which the fundus camera of the present invention shown in FIG. 1 is partially modified according to another embodiment.

In addition, as another embodiment, as shown in FIG. 2, by partially modifying the fundus camera of FIG. 1, the first linear polarizing filter 81 may be provided between the mirror 40 and the polarizing beam splitter 50 to implement a fundus camera. When the first linear polarizing filter 81 is provided between the mirror 40 and the polarizing beam splitter 50, the first linear polarizing filter 81 may be installed such that only the P-polarized light is incident on the polarizing beam splitter 50. Thus, the first linear polarizing filter 81 may be provided such that the P-polarized light is transferred to the objective lens 60 the most.

Meanwhile, in the fundus camera according to the present invention, the position of the first linear polarizing filter 81 is not limited to the above-described examples, and as long as the first linear polarizing filter 81 is positioned between the illumination unit 10 and the polarizing beam splitter 50, the position of the first linear polarizing filter 81 may be changed. That is, the position of the first linear polarizing filter 81 may be variously modified and changed such that the first linear polarizing filter 81 may be positioned between the non-polarizing beam splitter 13 and the diffusion lens 20, between the diffusion lens 20 and the central imaging mask 21, between the central imaging mask 21 and the illumination lens 30 to be described below, between the illumination lens 30 and the mirror 40 to be described below, or between the mirror 40 and the polarizing beam splitter 50.

Next, the second linear polarizing filter 82 is provided between the polarizing beam splitter 50 and the short-range eyepiece lens 70. In a direction away from the polarizing beam splitter 50, the size of the second linear polarizing filter 82 may be reduced, but in the direction away, the total optical path of the fundus camera manufactured according to the present invention is increased. In addition, in the fundus camera according to the present invention, the position of the second linear polarizing filter 82 is not limited to the above-described example, and as long as the second linear polarizing filter 82 is disposed between the polarizing beam splitter 50 and the imaging device 100, the position of the second linear polarizing filter 82 may be changed. That is, the second linear polarizing filter 82 may be disposed anywhere from a rear surface of the polarizing beam splitter 50 to a front surface of the imaging device 100 of the camera. For example, the second linear polarizing filter 82 may be disposed between the short-range eyepiece lens 70 and the imaging device 100.

A method of minimizing the size of the linear polarizing filter 80 is to attach the linear polarizing filter 80 to a front surface of the imaging device 100 included in the camera at a size corresponding to a size of the imaging device 100. For example, when the imaging device 100 has a diameter of 1 inch, the linear polarizing filter 80 may have a diameter of 1 inch, and when the imaging device 100 has a diameter of ½ inch, the linear polarizing filter 80 may have a diameter of ½ inch.

In FIG. 8A, as shown in a principle of the polarizing beam splitter 50, after the first linear polarizing filter 81 is positioned in front of the polarizing beam splitter 50, when the first linear polarizing filter 81 is positioned such that only light corresponding to the P-polarized light is transmitted, the largest amount of light is irradiated onto a retina, and when the first linear polarizing filter 81 is positioned such that only light corresponding to the S-polarized light is transmitted, light irradiated onto the retina is blocked. Accordingly, the first linear polarizing filter 81 is a device for controlling an amount of light and concurrently serves to irradiate only the pure P-polarized light onto a fundus.

In addition, when the P-polarized light passing through the polarizing beam splitter 50 is reflected and returned by an optical medium in front of the polarizing beam splitter 50, the P-polarized light is changed into the S-polarized light by a principle in which a phase of the P-polarized light is shifted by 180° and thus the P-polarized light is changed into the S-polarized light. Light changed into the S-polarized light is entirely reflected at 90° by the polarizing beam splitter 50 and may not enter a detector. Similarly, as diffused reflection occurs along various paths in a fundus which is an optical medium, some of light irradiated as P-polarized light is reflected as S-polarized light, and some thereof is reflected as P-polarized light so that only the P-polarized light passes through the polarizing beam splitter 50.

The P-polarized light passing through the polarizing beam splitter 50 may pass through the second linear polarizing filter 82 so that only a high-purity P-polarized retinal image may be transferred to the detector, and noise due to various reflections may be blocked with a high rejection ratio.

In other words, the first linear polarizing filter 81 and the second linear polarizing filter 82 may have the same polarity to transmit only high-purity P-polarized light. By definition of the term "high-purity", a rejection ratio of light orthogonal to the first linear polarizing filter 81 and the second linear polarizing filter 82 should be less than about 0.1% (<1/1,000) so that reflection shade disappears from a fundus photograph. This is because most CCD or complementary metal oxide semiconductor (CMOS) cameras have an analog-to-digital converter (ADC) resolution of 12 bits and should have a rejection ratio of 1/1,024 or less in order to reduce an error to a measurement error of 1 bit for digital image processing. To this end, before a product is released, it is necessary to confirm that an angle misalignment between the two linear polarizing filters 80 and the polarizing beam splitter 50 is within 2 to 6 rad (about 1.8 degrees).

As a material of the linear polarizing filter 80, a very thin film material and a square or rectangular glass material may all be used. The film material has an advantage of being thin and inexpensive but has a disadvantage of being easy to bend such as to change the entire optical property of the fundus camera and being deformed or damaged by heat. However, the film material has an advantage of being inexpensive.

Next, the objective lens 60 enlarges an image formed inside the fundus after the light incident from the polarizing beam splitter 50 enters the fundus. Next, the short-range eyepiece lens 70 reduces or enlarges the image of the fundus enlarged by the objective lens 60, and as a result, a user confirms the image of the fundus Next, the imaging device 100 may be an imaging sensor such as a monochrome CCD, a color CCD, or a color CMOS which has a quantum efficiency of 400 nm to 1,000 nm.

Figure 3:
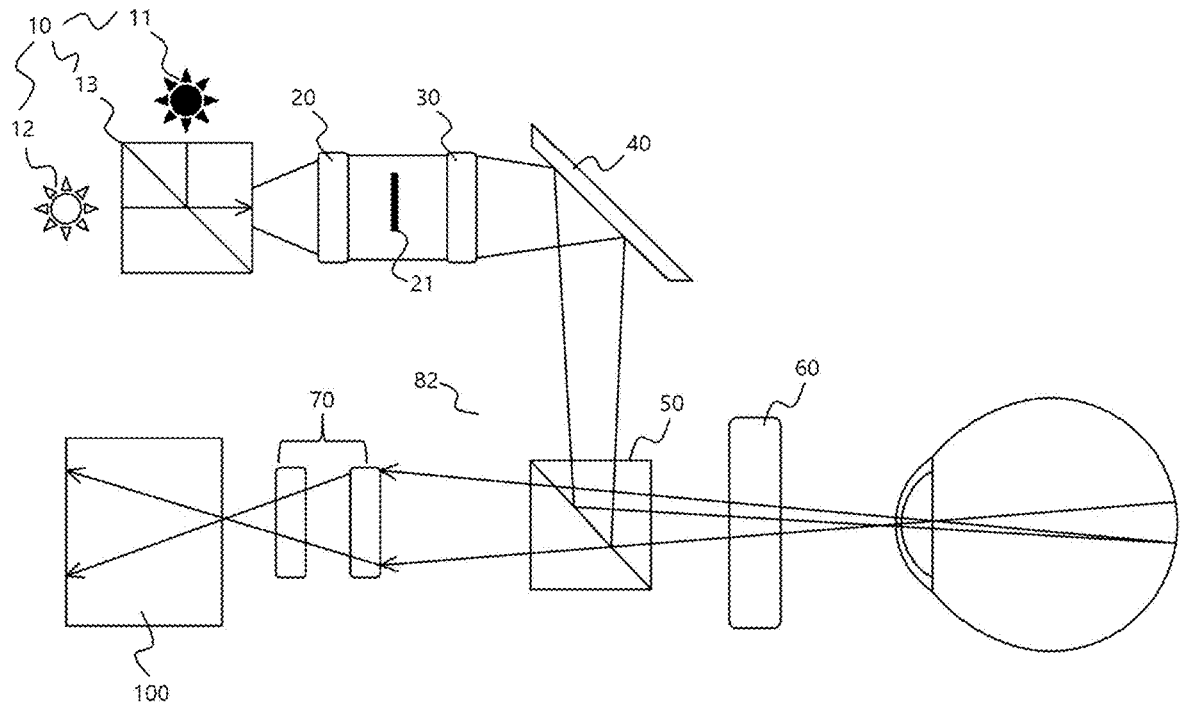
FIG. 3 is a view illustrating an example in which the fundus camera of the present invention shown in FIG. 1 is partially modified according to still another embodiment.

Meanwhile, as another embodiment, as shown in FIG. 3, the fundus camera of FIG. 1 may be partially modified to implement a fundus camera without the first linear polarizing filter 81 and the second linear polarizing filter 82. In this case, the polarizing beam splitter 50 may be implemented as a wire grid type beam splitter having a very high extinction ratio with respect to axes of the polarizing beam splitter that are orthogonal to each other. In this case, even without a linear polarizing filter, reflection shade caused by orthogonal light disappears from a fundus photograph by a polarizing beam splitter having a very high extinction ratio.

The present invention is a type of non-mydriatic fundus camera, which is a kind of diagnostic equipment for ophthalmic examination. A conventional fundus camera is a device that illuminates a fundus using a broadband illumination source in a visible ray band and records light reflected from the fundus using a film camera or an imaging device, but the present invention is a non-mydriatic fundus camera in which an illumination source configured to emit light having a near-infrared wavelength is added to illuminate a fundus in a non-mydriatic and to perform near-infrared ray fundus photographing first, and then an illumination source in a visible ray band is operated to sequentially record visible ray fundus photographs.

Figure 4:
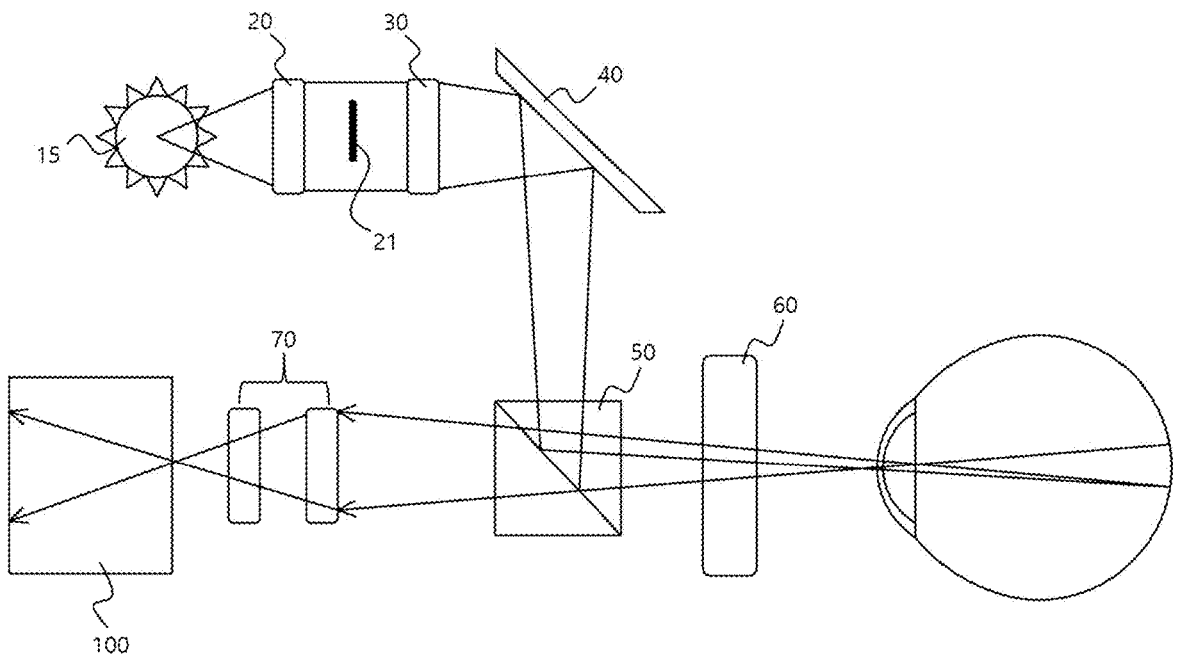
FIG. 4 is a view illustrating a basic configuration of a conventional coaxial illumination fundus camera.
Figure 5:
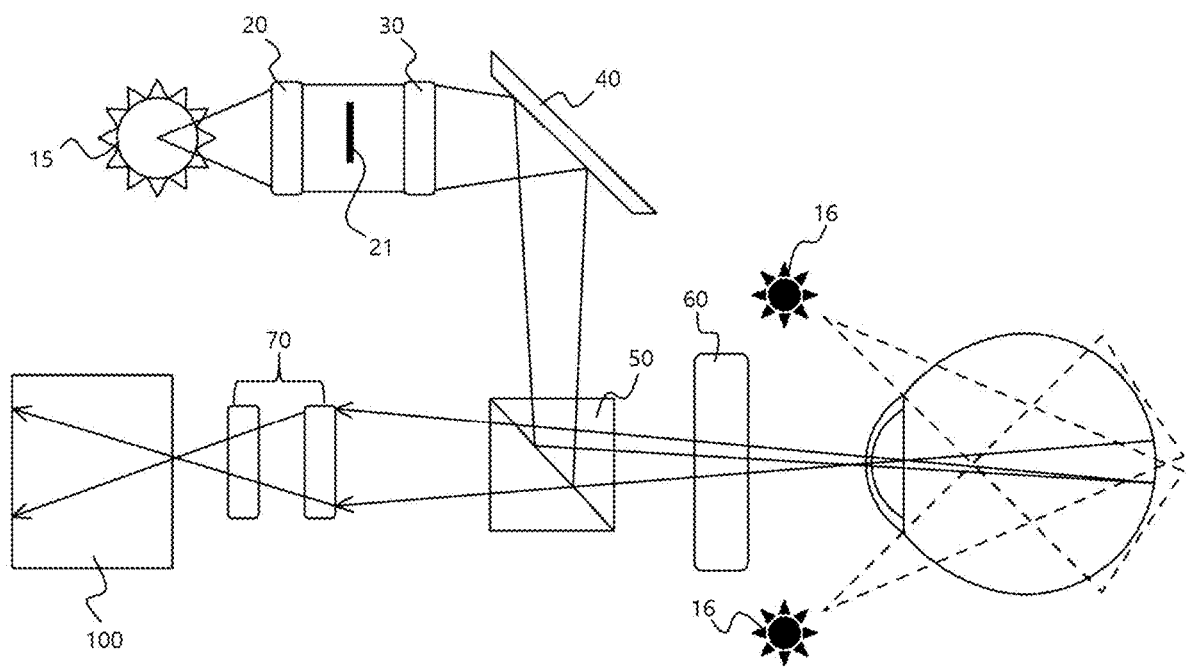
FIG. 5 is a view illustrating a basic configuration of another conventional coaxial illumination fundus camera.

FIG. 4 illustrates a basic configuration of a conventional coaxial illumination fundus camera. As shown in FIG. 4, unlike the case of the present invention, for example, only one visible ray illumination source is disposed as an illumination source 15. In this case, as shown in FIG. 5, since near-infrared ray illumination sources 16 are positioned around an objective lens 70 and a focus and a viewing angle are adjusted using light reflected from a retina after near-infrared ray illumination passes through a sclera or cornea, an unclear fundus photograph is acquired as compared with the present invention. In addition, light of the non-coaxial near-infrared ray illumination sources 15, which are not positioned coaxially, is reflected from the cornea and sclera, thereby degrading quality of a near-infrared ray fundus photograph. In addition, in order to photograph both left and right eyes using the non-coaxial near-infrared ray illumination sources, two illumination sources should be arranged around an objective lens, and thus, unlike the present invention in which a fundus may be illuminated using a single NIR, there is a problem in that costs and power consumption are increased due to use of two illumination sources. Meanwhile, the polarizing beam splitter 50 is a device which allows an image of an imaged fundus and illumination for imaging the fundus to be present on the same axis. However, in a conventional coaxial illumination fundus camera, a great deal of light is lost while passing through the polarizing beam splitter 50, and light noise caused by various reflections generated inside the polarizing beam splitter 50 enters a detector without being filtered.

Figure 6:
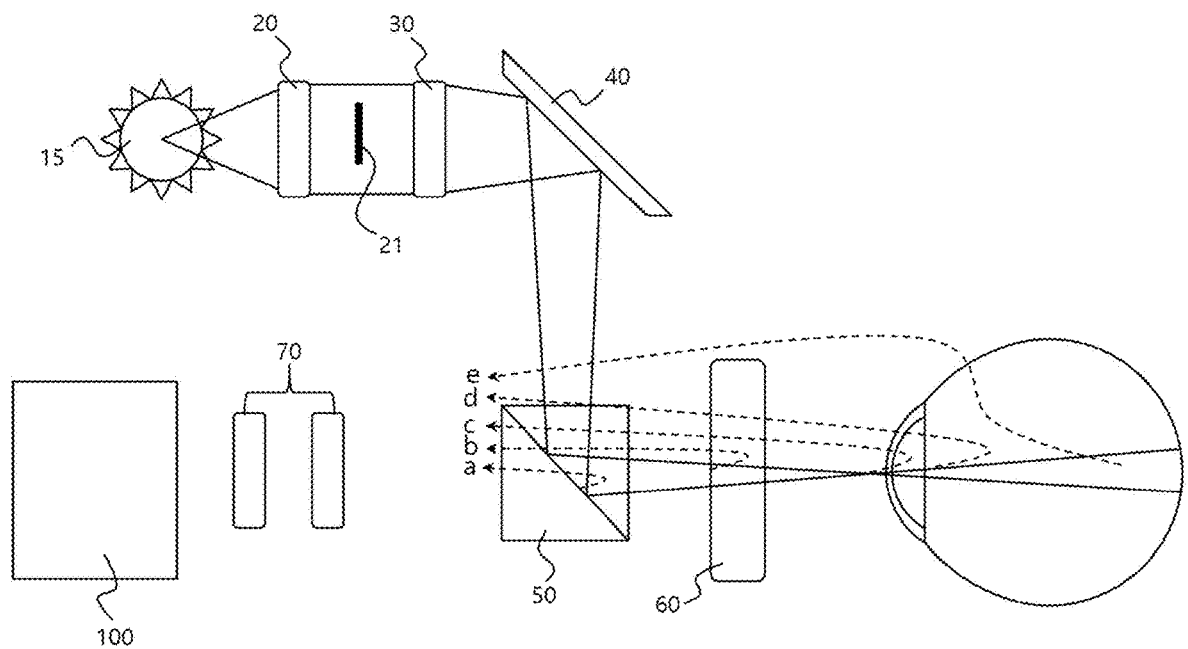
FIG. 6 is a view illustrating causes of various reflections occurring in the conventional coaxial illumination fundus cameras of FIGS. 4 and 5.

FIG. 6 illustrates causes and problems of various reflections that may occur in a conventional coaxial illumination fundus camera. An arrow a indicates reflection occurring in the polarizing beam splitter 50, and an arrow b indicates reflection occurring in the objective lens 60. An arrow c indicates reflection occurring in a cornea. An arrow d indicates reflection occurring in a crystalline lens. An arrow e indicates total reflection occurring in a vitreous body and a retina. Due to the reflections indicated by the arrows a to e, when a fundus photograph is captured, various reflection patterns appear, and thus, it is much confusing for a doctor to check a patient's fundus. In addition, when transmissivity to transmissibility of the polarizing beam splitter 50 is 50%, only half of light energy supplied from the polarizing beam splitter 50 is transferred to a fundus, and only half of light transferred from the fundus is transferred to a detector.

Figure 7:
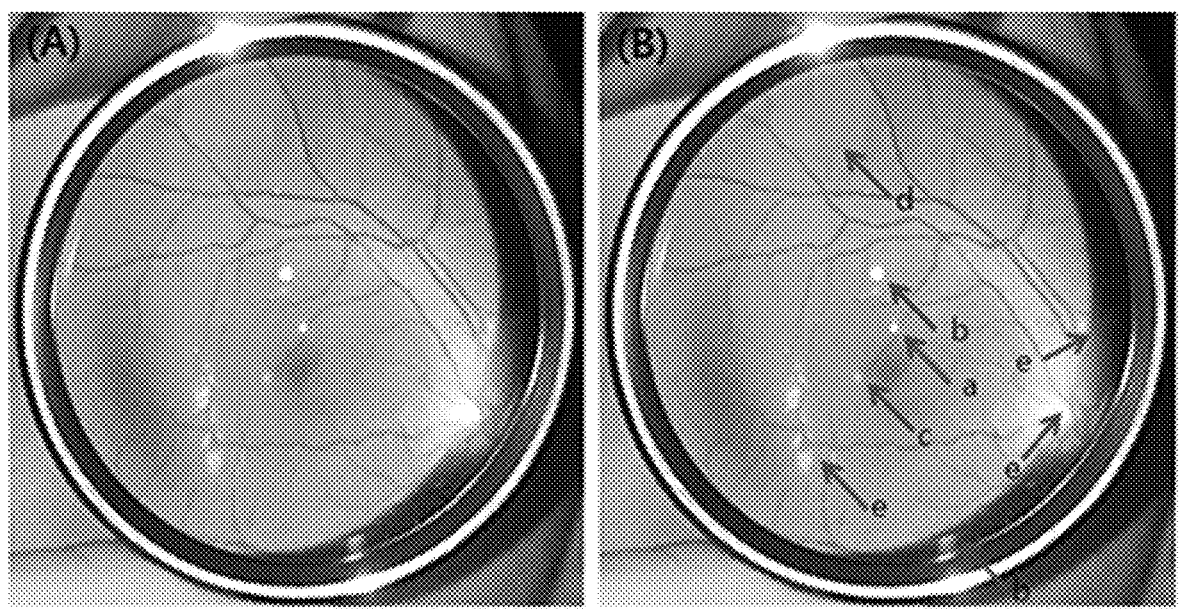
FIG. 7 shows fundus photographs captured using the conventional coaxial illumination fundus camera.

FIG. 7 shows fundus photographs captured using the conventional coaxial illumination fundus camera, and substances of the reflections shown in FIG. 6 may be confirmed through the fundus photographs. As in FIG. 6, an arrow a indicates reflection occurring in the polarizing beam splitter 50, and an arrow b indicates reflection occurring in the objective lens 60. An arrow c indicates reflection occurring in a cornea. An arrow d indicates reflection occurring in a crystalline lens. An arrow e indicates total reflection occurring in a vitreous body and a retina. When a position of a patient's eye or angles of an optical system and a visual axis are changed, patterns of the reflections indicated by the arrows a to e are unpredictably changed, and thus, the reflections may not be removed by software, thereby degrading a diagnostic value of equipment.

Figure 10:
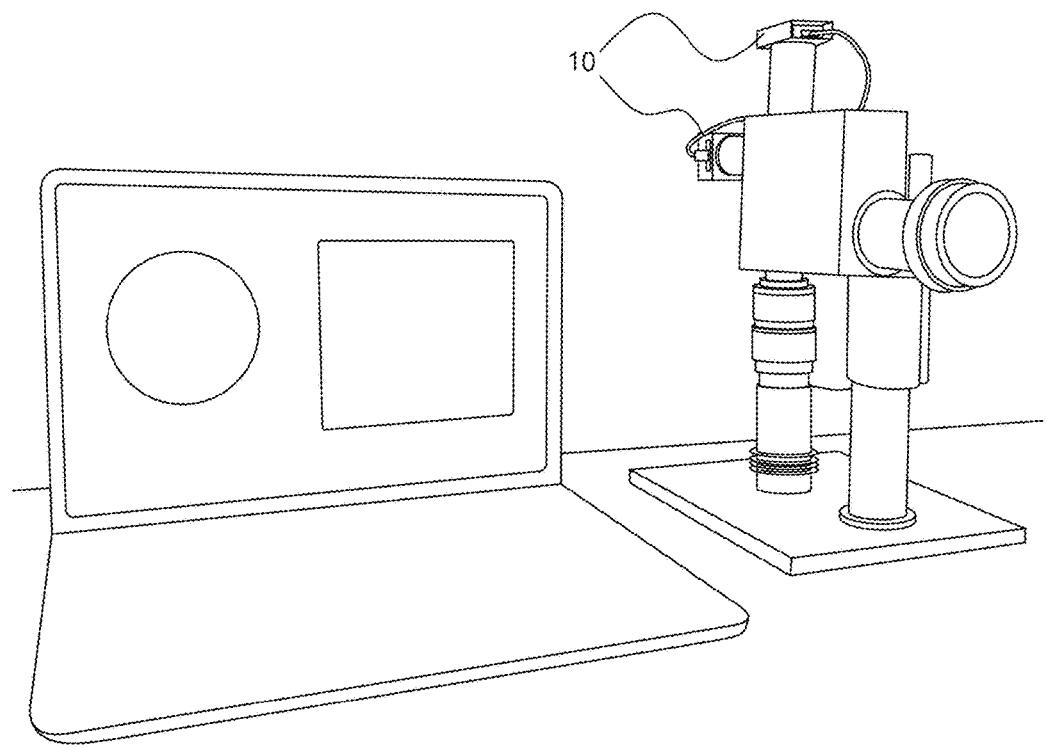
FIG. 10 illustrates a fundus camera manufactured according to one embodiment of the present invention.

In order to describe the present invention again, a coaxial non-mydriatic multispectral fundus camera, which is implemented using the near-infrared ray illumination source 11, the visible ray illumination source 12, and the non-polarizing beam splitter 13 manufactured according to the present invention, is shown in FIG. 10. Near-infrared ray fundus photographs captured using a near-infrared ray illumination source of the present invention are shown in FIG. 11.

According to the present invention, through a method of exchanging or moving the near-infrared ray illumination source 11 and/or the visible ray illumination source 12, according to a desired purpose, necessary illumination may be transferred to a fundus to acquire near-infrared ray and visible ray fundus photographs in a necessary band. In addition, the illumination unit 10 may concurrently transfer continuous broadband light and single narrowband light to the illumination axis and then image a fundus, thereby separating only necessary information on an imaging axis by using a bandpass optical filter.

In one embodiment, when a fundus is imaged using the near-infrared ray illumination source 11 having a wavelength of 740 nm and then a bandpass filter having a center wavelength of about 850 nm is used in front of the imaging device, a near-infrared ray self-fluorescent fundus camera may be easily implemented. Similarly, this can be applied to a visible light band, and when blue light having a wavelength ranging from 400 nm to 500 nm is irradiated onto a fundus from the visible ray illumination source 12 and a bandpass optical filter having a center wavelength ranging from 500 nm to 600 nm is used in front of the imaging device, a visible ray self-fluorescent fundus camera may be implemented.

Figure 11:
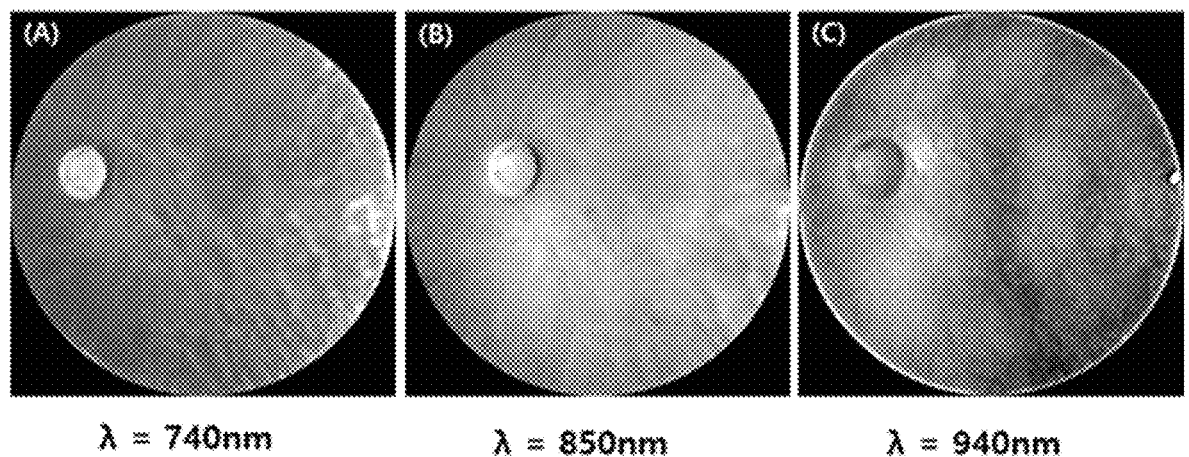
FIG. 11 shows choroidal fundus photographs captured using an replaceable illumination source having central emission wavelengths of 740 nm in FIG. 11A, 850 nm in FIG. 11B, and 940 nm in FIG. 11C of the fundus camera manufactured according to the present invention.

Near-infrared ray narrowband fundus photographs, which are acquired by photographing a fundus by replacing each of the near-infrared ray illumination source 11 and the visible ray illumination source 12 with an illumination source having a central wavelength of 740 nm, 850 nm, and 940 nm, and a full-width-at-half-maximum (FWHM) of 20 nm, are shown in FIG. 11.

In FIG. 11A, a shadow of a blood vessel, which is brightly imaged at a wavelength of 740 nm, corresponds to an image of a choroidal fundus photograph including an oxygen-rich choroidal artery. As shown in FIG. 11B, such a structure is inverted at a wavelength of 850 nm and is observed to be dark. In addition, in the near-infrared ray fundus photograph in of FIG. 11C, detailed structures not observed at the wavelengths of 740 nm and 850 nm are observed, which correspond to shades of choroidal capillaries. Accordingly, in the coaxial non-mydriatic multispectral fundus camera using the replaceable near-infrared ray illumination source and visible ray illumination source of the present invention, a fundus may be photographed by replacing the near-infrared ray illumination source 11 and/or the visible ray illumination source 12 according to a purpose.

In addition, a plurality of near-infrared ray illumination sources 11 and/or a plurality of visible ray illuminations sources 12 may be provided to be replaceable. The near-infrared ray illumination source 11 may include the plurality of near-infrared ray illumination sources 11 in different bands, each of the plurality of near-infrared ray illumination sources 11 may be detachable from the fundus camera, and one of the plurality of near-infrared ray illumination sources 11 may be replaced with another one of the plurality of near-infrared ray illumination sources 11. Similarly, the visible ray illumination source 12 may include the plurality of visible ray illumination sources 12 in different bands, each of the plurality of visible ray illumination sources 12 may be detachable from the fundus camera, and one of the plurality of visible ray illumination sources 12 may be replaced with another one of the plurality of visible ray illumination sources 12.

Figure 12:
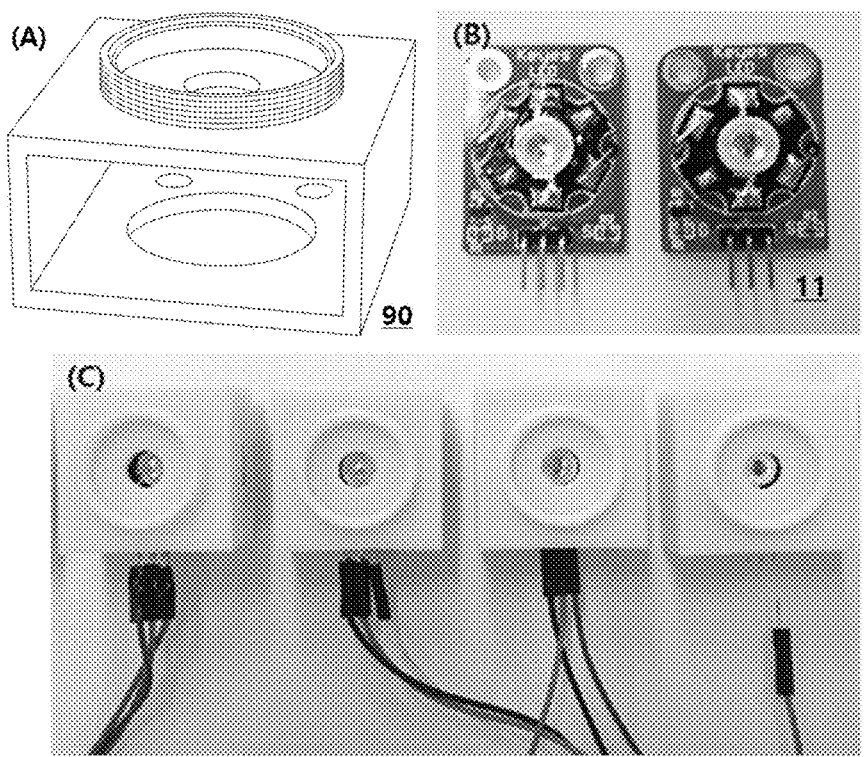
FIG. 12 shows an image showing an replaceable illumination source case 90 (FIG. 12A) manufactured according to one embodiment of the present invention, images (FIG. 12B) showing narrowband light-emitting diode illumination sources having wavelengths of 740 nm (left) and 850 nm (right) disposed on a heat sink, and images (FIG. 12C) showing near-infrared ray illumination sources equipped with light-emitting diodes having central emission wavelengths of 660 nm, 740 nm, 850 nm, and 940 nm from the left to right.

Additionally, as shown in FIG. 12A, the fundus camera according to the present invention may further include an illumination source case 90. The illumination source case 90 may be manufactured to have various shapes so as to be connected along an illumination axis. For example, as shown in FIGS. 12A and 12C, the illumination source case 90 may include a housing in which the near-infrared ray illumination source 11 or the visible ray illumination source 12 may be embedded. An opening may be formed in one surface of the housing, and thus, light from the near-infrared ray illumination source 11 or visible-ray illumination source 12 may be emitted from the opening to the illumination axis. The shape of the illumination source case 90 is not limited to that shown in FIG. 12A and is sufficient as long as the shape is connected to the illumination axis. The shape of the illumination source case 90 may be modified and changed into various shapes. As shown in FIG. 12C, the near-infrared ray illumination source 11 and/or the visible ray illumination source 12 may be mounted to be replaceable inside the illumination source cases 90.

For example, the near-infrared ray illumination source 11 may be provided with a plurality of near-infrared ray illumination sources 11 in different bands (see FIG. 12B). When the illumination source case 90 mounted with one near-infrared ray illumination source of the plurality of near-infrared ray illumination sources 11 is mounted in the fundus camera, the illumination source case 90 mounted with one near-infrared ray illumination source may be removed and replaced with the illumination source case 90 mounted with another near-infrared ray illumination source of the plurality of near-infrared ray illumination sources 11, and thus, the illumination source case 90 mounted with another near-infrared ray illumination source may be mounted in the fundus camera.

Similarly, the visible ray illumination source 12 may be provided with a plurality of visible ray illumination sources 12 in different bands. When the illumination source case 90 mounted with one visible ray illumination source of the plurality of visible ray illumination sources 12 is mounted in the fundus camera, the illumination source case 90 mounted with one visible ray illumination source may be removed and replaced with the illumination source case 90 mounted with another visible ray illumination source of the plurality of visible ray illumination sources 12, and thus, the illumination source case 90 mounted with another visible ray illumination source may be mounted in the fundus camera.

In addition, for example, the illumination source case 90 (see FIG. 10C) including the near-infrared ray illumination source 11 or the visible ray illumination source 12 may be manufactured to be coupled to the illumination unit 10 (for example, a case for fixing the non-polarizing beam splitter 13) in a thread manner. The illumination source case 90 mounted with the near-infrared ray illumination source 11 or the visible ray illumination source 12 may be manufactured in a male screw manner, and a portion of the illumination unit 10 (for example, the case for fixing the non-polarizing beam splitter 13), to which the illumination source case 90 is coupled, may be manufactured in a female screw manner. Thus, the illumination source case 90 being detachable from the illumination unit 10 may be an example.

FIG. 12B illustrates examples of narrowband light-emitting diode illumination sources (left: 740 nm and right: 850 nm) as the near-infrared ray illumination source 11. The near-infrared ray illumination source 11 may be mounted in the illumination source case 90, and as shown in FIG. 12C, a plurality of illumination source units may be manufactured using the illumination source case 90. FIG. 12C is an image when near-infrared ray illumination sources are manufactured by mounting light-emitting diodes having central emission wavelengths of 660 nm, 740 nm, 850 nm, and 940 nm from the left to right.

Such a principle is applied not only to the near-infrared ray illumination source 11 described above, but also to the visible ray illumination source 12, and thus, it is possible to use narrowband visible rays having various wavelengths such as 480 nm, 500 nm, 530 nm, 580 nm, and 620 nm or use a visible ray having a continuous spectrum ranging from 400 nm to 700 nm.

Figure 14:
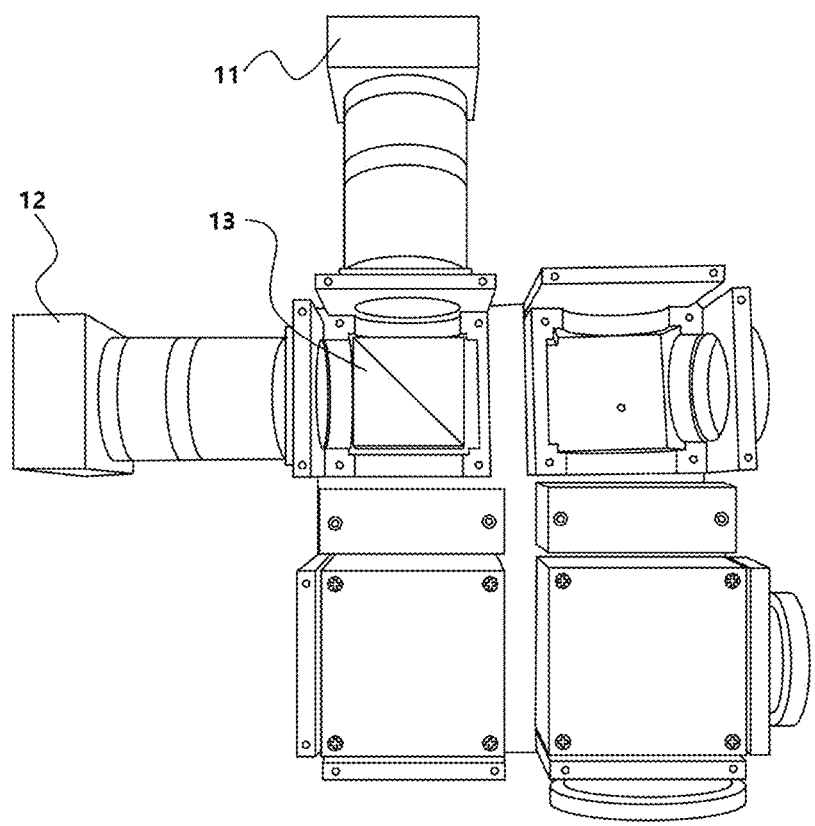
FIG. 14 illustrates a near-infrared ray illumination source (11), a visible ray illumination source (12), and a non-polarizing beam splitter (13) manufactured according to one embodiment of the present invention.

FIG. 14 illustrates the illumination unit 10 manufactured according to one embodiment of the present invention, that is, the near-infrared ray illumination source 11, the visible ray illumination source 12, and the non-polarizing beam splitter 13. In this case, as described above with reference to FIG. 12, FIG. 14 illustrates a case in which each of the near-infrared ray illumination source 11 and the visible ray illumination source 12 is embedded in the illumination source case 90 and thus is coupled to the non-polarizing beam splitter 13 (that is, the case for fixing the non-polarizing beam splitter 13).

Figure 15:
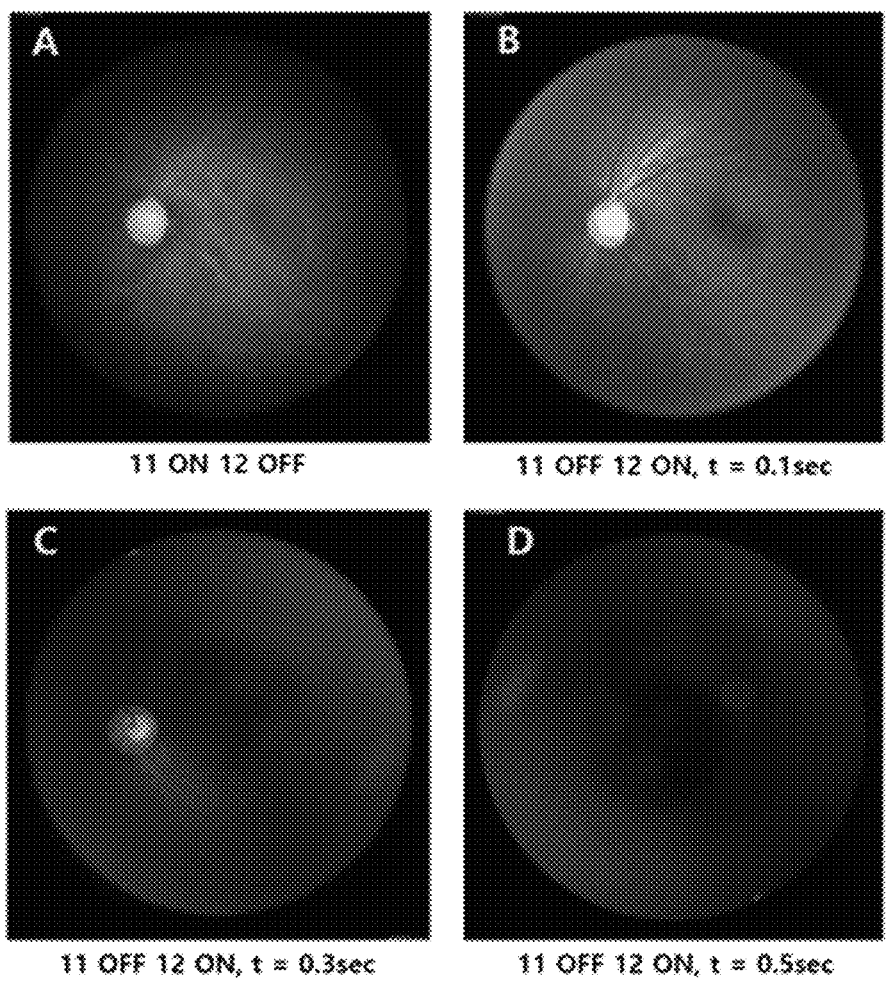
FIG. 15 shows photographic results of the non-mydriatic fundus camera manufactured according to the present invention, shows images (FIGS. 15A and 15B) acquired by controlling the near-infrared ray illumination source (11) and the visible ray illumination source (12), and shows examples of fundus photographs (FIGS. 15B, 15C, and 15D) changed over time, which are recorded in an imaging device (100) after the visible ray illumination source (12) is operated.

FIG. 15 shows photographic results of the non-mydriatic fundus camera manufactured according to the present invention, shows images of FIGS. 15A and 15B acquired by controlling the near-infrared ray illumination source 11 and the visible ray illumination source 12, and shows examples of fundus photographs of FIGS. 15B, C, and D changed over time, which are recorded in an imaging device after the visible ray illumination source 12 is operated.

Figure 16:
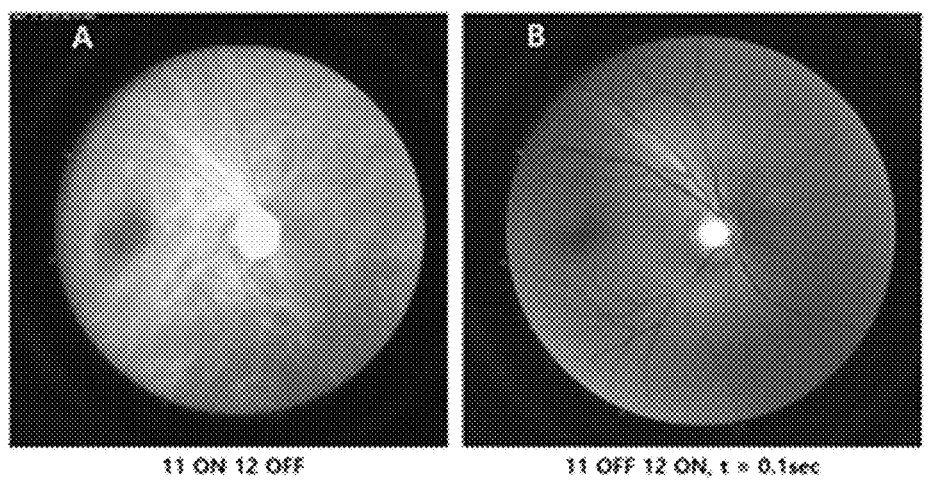
FIG. 16 shows photographic results of the non-mydriatic fundus camera manufactured according to the present invention and shows examples of fundus photographs of images (FIGS. 16A and 16B) acquired by controlling the near-infrared ray illumination source (11) and the visible ray illumination source (12), which are recorded in a black-and-white imaging device.

FIG. 16 shows photographic results of the non-mydriatic fundus camera manufactured according to the present invention and shows examples of fundus photographs of images of FIGS. 16A and 16B acquired by controlling the near-infrared ray illumination source 11 and the visible ray illumination source 12, which are recorded in a black-and-white imaging device.

Figure 17:
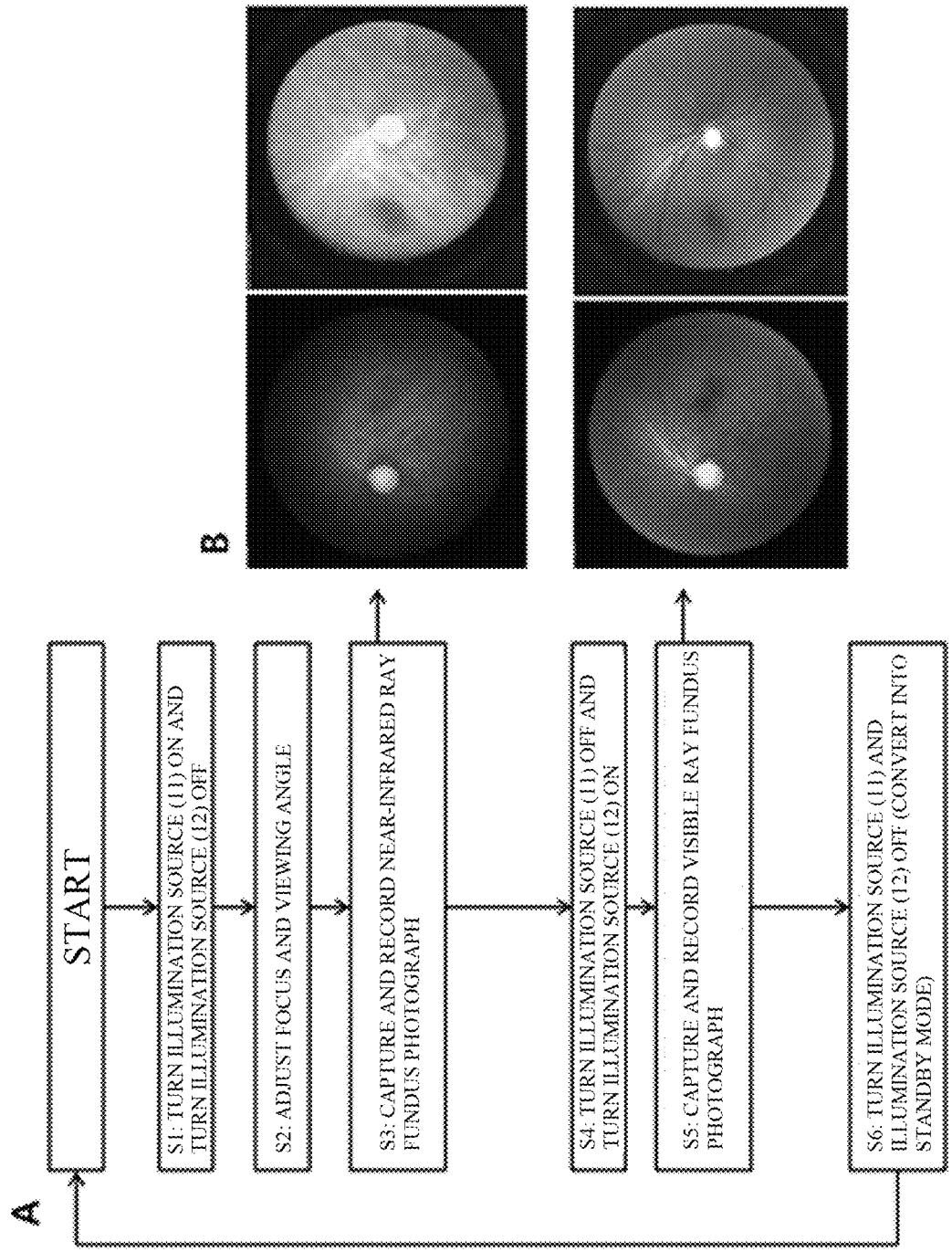
FIG. 17 is an operation flowchart of a method of acquiring a fundus photograph using a non-mydriatic fundus camera according to the present invention.

FIG. 17 is an operation flowchart of a method of acquiring a fundus photograph using a non-mydriatic fundus camera according to the present invention, FIG. 17A is a flowchart of sequentially acquiring a near-infrared ray fundus photograph and a visible ray fundus photograph in a standby mode, and FIG. 17B shows the near-infrared ray fundus photograph and the visible ray fundus photograph acquired in operations of the flowchart of FIG. 17B.

In the method of acquiring a fundus photograph using a fundus camera according to the present invention, first, operation S1 of setting a near-infrared ray illumination source 11 to be turned on and setting a visible ray illumination source 12 to be turned off may be performed. Next, operation S2 of imaging a fundus using the near-infrared ray illumination source 11 and adjusting a focus and a viewing angle is performed. Subsequently, operation S3 of acquiring the near-infrared ray fundus photograph by photographing the fundus in a state in which the fundus is imaged using the near-infrared ray illumination source 11 is performed.

Thereafter, operation S4 of setting the near-infrared ray illumination source 11 to be turned off and setting the visible ray illumination source 12 to be turned on is performed. Meanwhile, the fundus camera according to the present invention includes the near-infrared ray illumination source 11, the visible ray illumination source 12, and the non-polarizing beam splitter 13 as the illumination source 10 as described above, and the near-infrared ray illumination source 11 and the visible ray illumination source 12 are arranged coaxially due to the non-polarizing beam splitter 13. Therefore, without performing an operation of imaging the fundus using the visible ray illumination source 12 and adjusting a focus and a viewing angle, operation S5 of acquiring the visible ray fundus photograph by photographing the fundus in a state in which the fundus is imaged using the visible ray illumination source 12 may be performed subsequently to operation S4. Next, operation S6 of setting the visible ray illumination source 12 to be turned off is performed so that the fundus camera enters a standby mode, that is, the near-infrared ray illumination source 11 and the visible ray illumination source 12 are both in an off-state.

Figure 18:
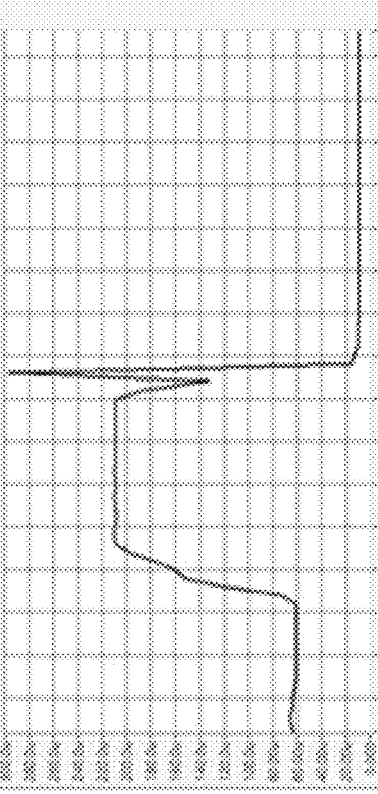
FIG. 18 is an example in which energy of an illumination source of the non-mydriatic fundus camera (FIG. 18A) manufactured according to the present invention and energy of an illumination source of a non-mydriatic fundus camera (FIG. 18B) sold by another company are measured on a retinal surface.
Figure 18:
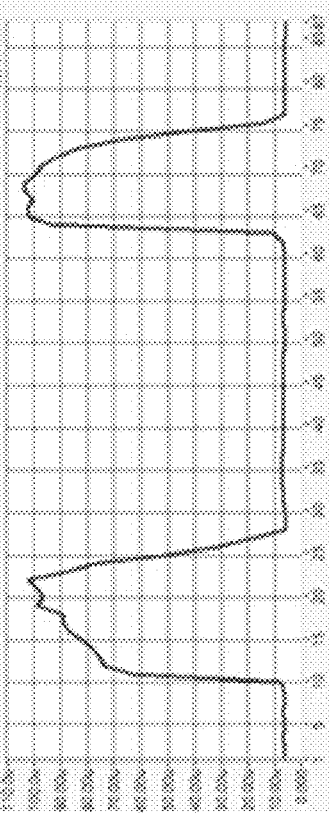

FIG. 18 is an example in which energy of an illumination source of the non-mydriatic fundus camera manufactured according to the present invention and energy of an illumination source of a non-mydriatic fundus camera sold by another company are measured on a retinal surface. In the case of the non-mydriatic fundus camera of another company using strong flash illumination so as to capture a color fundus photograph, the energy of the illumination source irradiated onto the fundus shows a sharp peak, but in the present invention, which does not use flash illumination, there is no difference in energy of the illumination source irradiated onto an eye during near-infrared ray imaging and visible ray imaging. As a result, incident energy of light irradiated onto an eye could be reduced to ⅓ (104.2 $\mu W/cm^2$ over 339.9 $\mu W/cm^2$).

In summary, as described above, in a conventional non-mydriatic color fundus camera, after a fundus in a non-mydriatic state is imaged using a near-infrared ray illumination source, a focus is adjusted, an adjustment is performed to align an imaging device with the fundus, and then, a fundus photograph is acquired using a xenon flash tube or other types of visible ray source to implement a non-mydriatic function. In such a conventional method, the near-infrared ray illumination source is placed around an objective lens, and a focus and a viewing angle before photographing are adjusted with light reflected from a retina after near-infrared ray illumination passes through a sclera or a cornea.

However, according to the present invention, since not only a visible ray illumination source but also a near-infrared ray illumination source are positioned coaxially, 1) a clear near-infrared ray fundus photograph can be acquired, 2) phototoxicity can be reduced by reducing a price and energy of light transferred to an eyeball using a small number of the near-infrared ray illumination sources, and 3) a color fundus photograph can be captured, of which a viewing angle and a focus match those of an image of a fundus imaged using an NIR.

In addition, according to the present invention, in a fundus camera using coaxial illumination, various types of internal reflections can be removed and a clear fundus photograph can be acquired using a combination of a polarizing beam splitter and two linear polarizing filters.

Furthermore, according to the present invention, light in a narrow spectral region can be emitted, and a visible light source and a near-infrared light source can be provided to be easily replaceable, and thus, a fundus photograph suitable for each lesion can be obtained using near-infrared light sources and visible light sources having various wavelengths.

In addition, a fundus can be effectively photographed at a wide angle without an expensive optical device or an expensive laser-based fundus imaging device so that the present invention can be usefully used for ophthalmologic treatment and non-mydriatic fundus cameras.

In addition, the present invention can be usefully used in photographing a fundus of an animal or in photographing a fundus of a child with whom cooperation is difficult.

As described above, those skilled in the art to which the present invention pertains will understand that the present invention may be implemented in other detailed forms without departing from the technical spirit or essential characteristics of the present invention.

Accordingly, the aforementioned embodiments should not be construed as being limitative, but should be construed as being only illustrative in all aspects. Furthermore, the scope of the present invention is defined by the appended claims rather than the detailed description, and it should be understood that all modifications or variations derived from the meanings and scope of the present invention and equivalents thereof are included in the scope of the appended claims.

The invention claimed is:

1. A coaxial non-mydriatic multispectral fundus camera using a near-infrared ray illumination source and a visible ray illumination source, comprising:
    an illumination unit configured to emit light;
    a diffusion lens configured to diffuse the light incident from the illumination unit;
    an illumination lens configured to irradiate the light incident from the diffusion lens at a predetermined emission angle;
    a mirror configured to reflect the light incident from the illumination lens;
    a polarizing beam splitter configured to transmit P-polarized light of the light incident from the mirror and reflect S-polarized light thereof;
    an objective lens configured to image a fundus using the light incident from the polarizing beam splitter and then enlarge a returning image of the fundus;
    a short-range eyepiece lens configured to reduce or enlarge the image of the fundus enlarged by the objective lens; and
    an imaging device configured to acquire a fundus photograph from the image of the fundus received from the short-range eyepiece lens,
    wherein the illumination unit includes:
        a near-infrared ray illumination source configured to emit a near-infrared ray;
        a visible ray illumination source configured to emit a visible ray; and
        a non-polarizing beam splitter located between the near-infrared ray illumination source and the diffusion lens and between the visible ray illumination source and the diffusion lens and configured to allow the near-infrared ray emitted from the near-infrared ray illumination source and the visible ray emitted from the visible ray illumination source to be emitted coaxially, wherein the near-infrared ray illumination source emits the near-infrared ray toward the non-polarizing beam splitter in a first direction and the visible ray illumination source emits the visible ray toward the non-polarizing beam splitter in a second direction perpendicular to the first direction, and
    wherein coaxial non-mydriatic multispectral fundus camera further comprises: a central imaging mask located between the diffusion lens and the illumination lens and configured to reduce the light incident on a coaxial center of an illumination axis so as to minimize a corneal reflex and to prevent the light from being incident around an apical convex surface of a central part of a cornea, the central imaging mask including a hollow cylinder, a central mask located inside the hollow cylinder to block the light incident on the coaxial center, and spiders supporting the central mask to the hollow cylinder.

2. The coaxial non-mydriatic multispectral fundus camera of claim 1, wherein, when, with respect to the non-polarizing beam splitter, the near-infrared ray illumination source is disposed perpendicularly to the illumination axis and the visible ray illumination source is disposed on the illumination axis, the non-polarizing beam splitter reflects the near-infrared ray emitted from the near-infrared ray illumination source and transmits the visible ray emitted from the visible ray illumination source, and
    when, with respect to the non-polarizing beam splitter, the near-infrared ray illumination source is disposed on the illumination axis and the visible ray illumination source is disposed perpendicularly to the illumination axis, the non-polarizing beam splitter transmits the near-infrared ray emitted from the near-infrared ray illumination source and reflects the visible ray emitted from the visible ray illumination source.

3. The coaxial non-mydriatic multispectral fundus camera of claim 1, wherein the near-infrared ray illumination source is a light-emitting diode or a narrowband single wavelength laser which emits a narrowband near-field ray in a range of 700 nm to 1,000 nm.

4. The coaxial non-mydriatic multispectral fundus camera of claim 1, wherein the visible ray illumination source is a narrowband visible light source or a narrowband single wavelength laser which emits a narrowband visible ray in a range of 400 nm to 700 nm, or a visible light-emitting diode having a continuous spectrum ranging from 400 nm to 700 nm.

5. The coaxial non-mydriatic multispectral fundus camera of claim 1, wherein the near-infrared ray illumination source is provided with a plurality of near-infrared ray illumination sources in different bands, and
    each of the plurality of near-infrared ray illumination sources is detachable from the coaxial non-mydriatic multispectral fundus camera so that one of the plurality of near-infrared ray illumination sources is replaceable with another one of the plurality of near-infrared ray illumination sources.

6. The coaxial non-mydriatic multispectral fundus camera of claim 1, wherein the visible ray illumination source is provided with a plurality of visible ray illumination sources in different bands, and
    each of the plurality of visible ray illumination sources is detachable from the coaxial non-mydriatic multispectral fundus camera so that one of the plurality of visible ray illumination sources is replaceable with another one of the plurality of visible ray illumination sources.

7. The coaxial non-mydriatic multispectral fundus camera of claim 5, further comprising an illumination source case which includes a housing in which the near-infrared ray illumination source is embedded and is detachable from the coaxial non-mydriatic multispectral fundus camera,
    wherein an opening is formed in one surface of the housing so that light from the near-infrared ray illumination source is emitted from the opening to an illumination axis, and
    the illumination source case, which is mounted with one of the plurality of near-infrared ray illumination sources and is mounted in the coaxial non-mydriatic multispectral fundus camera, is replaceable with the illumination source case mounted with still another one of the plurality of near-infrared ray illumination sources.

8. The coaxial non-mydriatic multispectral fundus camera of claim 6, further comprising an illumination source case which includes a housing in which the visible ray illumination source is embedded and is detachable from the coaxial non-mydriatic multispectral fundus camera,
   wherein an opening is formed in one surface of the housing so that light from the visible ray illumination source is emitted from the opening to an illumination axis, and
   the illumination source case, which is mounted with one of the plurality of visible ray illumination sources and is mounted in the coaxial non-mydriatic multispectral fundus camera, is replaceable with the illumination source case mounted with still another one of the plurality of visible ray illumination sources.

9. The coaxial non-mydriatic multispectral fundus camera of claim 1, further comprising at least one of a first linear polarizing filter configured to transmit only the P-polarized light and provided between the illumination unit and the polarizing beam splitter and a second linear polarizing filter provided between the polarizing beam splitter and the imaging device.

10. The coaxial non-mydriatic multispectral fundus camera of claim 1, further comprising:
    a first linear polarizing filter configured to transmit only the P-polarized light and provided between the illumination unit and the polarizing beam splitter; and
    a second linear polarizing filter provided between the polarizing beam splitter and the imaging device,
    wherein the first linear polarizing filter and the second linear polarizing filter have the same polarity to transmit only high-purity P-polarized light.

* * * * *